United States Patent [19]

Kramer et al.

[11] Patent Number: 5,616,459
[45] Date of Patent: Apr. 1, 1997

[54] SELECTION OF RIBOZYMES THAT EFFICIENTLY CLEAVE TARGET RNA

[75] Inventors: Fred R. Kramer, Riverdale; David Dubnau; Karl A. Drlica, both of New York; Abraham Pinter, Brooklyn, all of N.Y.

[73] Assignee: The Public Health Research Institute of the City of New York, Inc., New York, N.Y.

[21] Appl. No.: 931,560

[22] Filed: Aug. 18, 1992

Related U.S. Application Data

[63] Continuation of Ser. No. 553,729, Jul. 16, 1990, abandoned.
[51] Int. Cl.[6] .............................. C12Q 1/70; C12Q 1/68; C07H 21/02
[52] U.S. Cl. .................................. 435/5; 435/6; 536/23.2
[58] Field of Search .............................. 435/5, 6, 29, 32, 435/34; 436/63, 501; 935/77

[56] References Cited

U.S. PATENT DOCUMENTS

| | | | |
|---|---|---|---|
| 4,680,265 | 7/1987 | Birmingham et al. | 435/172.3 |
| 5,037,746 | 8/1991 | Cech et al. | 435/91 |
| 5,144,019 | 9/1992 | Rossi et al. | 536/23.1 |

OTHER PUBLICATIONS

Albano et al. "Nucleotide Sequence and Genetic Organization of the Bacillus Subtilis comG Operon", J. Bacteriology, vol. 171, Oct. 1989, pp. 5386–5404.
Cameron, F. et al., "Specific Gene Suppression by Engineered Ribozymes in Monkey Cells", Proc. National Academy of Science USA, vol. 86, Dec. 1989, pp. 9139–9143.
Cotten, M., et al. "Ribozyme, Antisense RNA, and Antisense DNA Inhibition of U7 Small Nuclear Ribonucleoprotein –Mediated Histone Pre–mRNA Processing in Vitro":, Mol. Cell. Biol., vol. 9, Oct. 1989, pp. 4479–4487.
Dubnau, D., "Translational Attenuation: The Regulation of Bacterial Resistance to the Macrolide–Lincosamide–Streptogramin B antibiotics", CRC Critical Rev. Biochem, vol. 16, 1984, pp. 103–132.
Fedor, M.J., et al., "Substrate Sequence Effects on Hammerhead RNA Catalytic Efficiency.", Proc. Natl. Acad. Sci., USA, vol. 87, Mar. 1990, pp. 1668–1672.
Forster, A.C., et al., "Self–Cleavage of Virusoid RNA is performed by the Proposed 55–Nucleotide Active Site", Cell, vol. 50, Jul. 1987, pp. 9–16.
Forster, A.C., et al., "Self Cleavage of Plus and Minus RNA's of a Virusoid and a Structural Model for the Active Sites", Cell, vol. 49, Apr. 1987, pp. 211–220.
Gryczan, T.J., et al., "Conformational Alteration of mRMA Structure and the Posttranscriptional Regulation of Erythromycin–Induced Drug Resistance", Nucleic Acids Res., vol. 8, 1980, pp. 6081–6097.
Hampel, A., et al., "RNA Catalytic Properties of the Minimum (=) sTRSV Sequence", Biochemistry, vol. 28, Jun. 1989, pp. 4929–4933.

Hampel, A., et al., "'Hairpin' Catalytic RNA model: Evidence for Helices and Sequence Requirement for Substrate RNA", Nucleic Acids Research, vol. 18, Jan. 1990, pp. 299–304.
Haseloff, J., et al., "Simple RNA Enzymes with New and Highly Specific Endoribo Nuclease Activities", Nature, vol. 334, Aug. 1988, pp. 585–591.
Heus, Hans A., et al., "Sequence–Dependent Structural Variations of Hammerhead RNA Enzymes", Nucleic Acids Res., vol. 18, Mar. 1990, pp. 1103–1108.
Kramer, F.R., et al., "Secondary Structure Formation During RNA Synthesis", Nucleic Acids Res., vol. 9, Oct. 1981, pp. 5109–5124.
Mayford, M., et al., "ermC. Leader Peptide Amino Acid Sequence Critical for Induction by Translational Attenuation", J. Mol. Biol., vol. 206, Mar. 1989, pp. 69–79.
Mayford, M., et al., "Conformational Alterations in the emrC Transcript in Vivo During Induction", EMBO J., vol. 8, Dec. 1989, pp. 4307–4314.
Narayanan, C.S., et al., "Evidence for the Translational Attenuation Model: Ribosome Binding Studies and Structural Analysis with an In Vitro Run–off Transcript of ermC", Nucleic Acids Res., vol. 13, Oct. 1985, pp. 7507–7326.
Sarver, N., et al., "Ribozymes as Potential Anti–HIV–1 Therapeutic Agents", Science, vol. 247, Mar. 1990, pp. 1222–1225.
Shivakumar, A.G., et al., "Posttranscriptional Regulation of an Erythromycin Resistance Protein Specified by Plasmid pE194", Proc. Nat'l. Acad. Sci. USA. vol. 77, Jul. 1980, pp., 3903–3907.
Shivakumar, A.G., et al., "Characterization of a Plasmid –Specified Ribosome Methylase Associated with Macrolide Resistance", Nucleic Acids Res., vol. 9, Jun. 1981, pp. 2549–2562.
Uhlenback, O.C., "A Small Catalytic Oligoribonucleotide", Nature, vol. 823, Aug. 1987, pp. 596–600.
Adachi, A., Gendelman, H., Koenig, S., Folks, T., Willey, R., Rabson, A. & Martin, M. (1986). "Production of acquired immunodeficiency syndrome–associated retrovirus in human and nonhuman cells transfected with an infectious molecular clone." J. Virol. 59, 284–291.
Contente, S., & Dubnau, D. (1979). "Characterization of plasmid transformation in *Bacillus subtilis*: kinetic properties and the effect of DNA conformation." Mol. Gen. Genet. 167, 251–258.
Dower, W.J., Miller, J.F., & Ragsdale, C. W. (1988) "High effiency transformation of E. coli by high voltage electroporation." Nucleic Acids Res. 16, 6127–6145.

(List continued on next page.)

Primary Examiner—Stephanie W. Zitomer
Assistant Examiner—Eggerton Campbell
Attorney, Agent, or Firm—William J. Hone

[57] ABSTRACT

Mutant ribozymes are screened by culturing cells whose survival is dependant upon cleavage of RNA by a ribozyme, which cleavage causes the cells to survive in the presence of an agent which otherwise would kill the cells, and selecting cells which survive.

55 Claims, 8 Drawing Sheets

OTHER PUBLICATIONS

Hofemeister, J., Israeli–Reches, M., & Dubnau, D. (1983). "Integration of plasmid pE194 at multiple sites on the *Bacillus subtilis* chromosome." mol. Gen. Genet. 189, 58–68.

Hutchison III, C.A., Nordeen, S.K., Vogt, K., & Edgell, M. H. (1986). "A complete library of point substitution mutations in the glucocorticoid response element of mouse mammary tumor virus." Proc. Natl. Acad. Sci. USA 83, 710–714.

Hutchins, C.J., Rathjen, P.D., Forster, A.C., & Symons, R.H. (1986). "Self–cleavage of plus and minus RNA transcripts of avacado sunblotch viroid." Nucleic Acids Res. 14, 3627–3640.

Jaeger, J.A., Turner, D.H., & Zuker, M. (1989). "Improved predictions of secondary structures for RNA." Proc. Natl. Acad. Sci. USA 86. 7706–7710.

James, A.A., Morrison, P.T., & Kolodner, R. (1982). "Genetic recombination of bacterial plasmid DNA. Analysis of the effect of recombination–deficient mutations on plasmic recombination." J. Mol. Biol. 160, 411–430.

Kacian, D.L., Mills, D.R., Kramer, F.R., & Spiegelman, S. (1972). "A replicating RNA molecule suitable for a detailed analysis of extracellular evolution and replication." Proc. Natl. Acad. Sci. USA 69, 3038–3042.

Kruger, K., Grabowski, P.J., Zaug, A.J., Sands, J., Gottschling, D.E., & Cech, T.R. (1982). "Self–splicing RNA: autoexcision and autocyclization of the ribosomal RNA intervening sequence of Tetrahymena." Cell 31, 147–157.

Lai, C.J., Dahlberg, J.E., & Weisblum, B. (1973). "Structure of an inducibly methlatable nucleotide sequence in 23S ribosomal ribonucleic acid from erythromycin–resistant *Staphylococcus aureus*." Biochemistry 12, 457–460.

Mao, J.C. H., & Robishaw, E.E. (1971). "Effects of macrolides on peptide–bond formation and translocation." Biochemistry 10, 2054–2061.

Mao, J.C.H., & Robinshaw, E.E. (1972). "Erythromycin, a peptidyltransferase effector." Biochemistry 11, 4864–4872.

Melton, D. A., Krieg, P.A., Rebagliati, M.R., Maniatis, T., Zinn, K., & Green, M.R. (1984). "Efficient in vitro synthesis of biologically active RNA and RNA hybridization probes from plasmids containing a bacteriophage SP6 promoter." Nucleic Acids Res. 12, 7035–7056.

Miele, E.A., Mills, D.R., & Kramer, F.R. (1983). "Autocatalytic replication of a recombinant RNA." J. Mol. Biol. 171, 281–295.

Milligan, J.F., Groebe, D.R., Witherall, G.W., & Uhlenbeck, O. C. (1987). "Oligonucleotide synthesis using T7 RNA polymerase and synthetic DNA templates." Nucleic Acids Res. 15, 8783–8798.

Mills, D.R., Kramer, F.R., & Spiegelman, S. (1973). "Complete nucleotide sequence of a replicating RNA molecule." Science 180, 916–927.

Prody, G.A., Bakos, J.T., Buzayan, J.M., Schneider, I.R., & Bruening, G. (1986). "Autolytic processing of dimeric plant virus satellite RNA." Science 231, 1577–1580.

Shine, J., & Dalgarno, L. (1974). "The 3'–terminal sequence of *Escherichia coli* 16S ribosomal RNA: complementarity to nonsense triplets and ribosome binding sites." Proc. Natl. Acad. Sci. USA 71, 1342–1346.

Tomizawa, J., & Itoh, T. (1981). "Plasmid ColE1 incompatability determined by interaction of RNAI with primer transcript." Proc. Natl. Acad. Sci. USA 78, 6096–6100.

Weisblum, B. Siddhikol, C., Lai, C.J., & Demohn, V. (1971). "Erythromycin–inducible resistance in *Staphyloccoccus aureus*: requirements for induction." J. Bacteriol. 106, 835–847.

Weisblum, B., Graham, M.Y., Gryczan, T., & Dubnau, D. (1979). "Plasmid copy number control: isolation and characterization of high–copy–number mutants of plasmid pE194." J. Bacteriol. 137, 635–643.

Yansura, D.G. & Henner, D.J. (1984). "Use of the *Escherichia coli* lac repressor and operator to control gene expression in *Bacillus subtilis*." Proc. Natl. Acad. Sci. USA 81, 439–443.

Zuker, M. (1989). "On finding all suboptical foldings of an RNA molecule." Science 244, 48–52.

Zuker, M. and Stiegler, P. (1981). "Optimal computer folding of large RNA sequences using thermodynamics and auxillary information. " Nucleic Acids Res. 9, 133–148.

Been, M.D. and Cech, T.R., "One Binding Site Determines Sequence Specificity of Tetrahymena Pre–rRNA Self–Splicing, Trans–Splicing, and RNA Enzyme Activity" Cell, vol. 47, Oct. 24, 1986, pp. 207–216.

Chuat et al, Biochem. Biophy. Res. Comm 162: 1025–1029 (1989).

Mirabelli et al, Anti–Cancer Drug Design 6:647–661 (1991).

Uhlman et al Chemical Reviews 90:544–576 (1990).

Murphy et al., Proc. Nat. Acad. Sci. USA, 86:9218–9222 (1989), "Attenation of substrate specificity . . . ".

Doudna et al., Proc. Nat. Acad. Sci. USA, 86:7402–7406 (1989) "RNA structure, not sequence, . . . ".

Murphy et al. Proc Natl Acad Sci USA, 86, 9218–9222 Dec. 1989.

SELECTION OF RIBOZYMES THAT EFFICIENTLY CLEAVE TARGET RNA

This application is a continuation of Ser. No. 07/553,729, filed Jul. 16, 1990, which is now abandoned.

FIELD OF THE INVENTION

This invention relates to the screening of ribozymes to determine which are most efficient at cleaving a target ribonucleic acid. The invention also relates to the generation of a variety of mutant ribozymes for screening.

BACKGROUND OF THE INVENTION

Certain naturally occurring RNA molecules undergo self-catalyzed cleavage (Kruger et al., 1982). The best studied examples occur in plants that are infected with viroids (Hutchins et al., 1986), virusoids (Forster & Symons, 1987a), or satellite viruses (Prody et al., 1986). The genomic RNAs of these infectious agents are reproduced by a rolling circle mechanism that yields multimeric replication intermediates that undergo self-cleavage to produce monomeric genomes. The ability to self-cleave is imparted by distal consensus sequences that interact to form a highly structured RNA configuration (in the form of a "hammerhead") prior to cleavage (Forster & Symons, 1987a, Forster & Symons, 1987b). Although self-cleavage is entirely intramolecular, a careful analysis of the sequences and structures involved led Uhlenbeck to the realization that a synthetic RNA could be constructed that would interact with a second RNA (the "substrate" strand) to form the hammerhead configuration, resulting in the cleavage of the substrate at a specific site (Uhlenbeck, 1987). He demonstrated that these synthetic RNAs act enzymatically.

Uhlenbeck's experiments raised the prospect that RNA enzymes ("ribozymes") could be constructed that would cleave a preselected sequence in any RNA. However, in his scheme some of the consensus sequences which were required to form the active hammerhead configuration were supplied by the substrate strand, severely limiting the number of natural RNAs that could serve as substrates. Haseloff and Gerlach markedly improved Uhlenbeck's design by including all the required consensus sequences in the ribozyme (Haseloff & Gerlach, 1988). Their ribozyme works by first hybridizing to a particular site in the substrate RNA and then catalyzing the cleavage of the substrate at that site. They disclose that sites containing the trinucleotide GUC, and perhaps GUU or GUA, are cleaved, provided that the structures present in the substrate RNA do not prevent the binding of the ribozyme to the site. FIG. 1A shows a typical Haseloff-Gerlach ribozyme hybridized to a substrate strand. The arrow indicates the site in the substrate where cleavage will occur. This site is immediately adjacent to the GUC sequence.

Haseloff-Gerlach ribozymes possess two different functional regions. The first functional region is a "catalytic domain" in the middle of the ribozyme (FIG. 1B), which contains the consensus sequences that confer the ability to cleave the substrate. The catalytic domain is example shown is 22 nucleotides-long. This region is common to Haseloff-Gerlach ribozymes. The second functional region consists of sequences on both sides of the catalytic domain. These sequences are chosen to be complementary to the sequences surrounding the cleavage site in the substrate (FIG. 1C). They confer upon the ribozyme the ability to interact specifically with a preselected cleavage site. Because the combined length of these complementary sequences is typically between 12 and 16 nucleotides, the Haseloff-Gerlach ribozymes are highly specific.

Experiments that tested the activity of Haseloff-Gerlach ribozymes in vivo have been disappointing. The expression of targeted gene products was not eliminated, but only reduced (Cameron & Jennings, 1989), and extremely high levels of ribozyme were required to destroy the intended substrate RNA (Cotten et al., 1989). Furthermore, our own in vitro studies showed that the optimal conditions for ribozyme activity (60 degrees Celsius in the presence of 40 mM magnesium chloride) are quite different from the conditions present in most eukaryotic cells. Naturally occuring hammerhead configurations are optimal only for cleavage within the same RNA (cleavage in cis). Moreover, in plant cells (where hammerheads normally function), cleavage might be aided by accessory proteins. The Haseloff-Gerlach ribozymes, on the other hand, are designed to cleave another RNA (cleavage in trans), without the benefit of cellular proteins. Furthermore, the Haseloff-Gerlach ribozymes might be particularly sensitive to cellular nucleases. It is thus not surprising that artificial ribozymes function less than optimally in vivo. The utility of therapeutic ribozymes will depend on their ability to function efficiently in a complex cellular milieu (Sarver et al., 1990). Thus, it is clear from our own work and from the work of other laboratories that the efficiency of ribozymes as currently designed, either Haseloff-Gerlach or other, is too low for them to serve as commercially effective therapeutic agents. A purpose of the invention described herein is to design and screen ribozymes that will efficiently cleave target RNA.

SUMMARY OF THE INVENTION

By utilizing cells whose survival in the presence of an agent depends on the activity of an expressed ribozyme, we have invented a method for selecting mutant ribozymes that function efficiently under physiological conditions. Our method for screening ribozymes comprises culturing cells whose survival is dependent upon cleavage of RNA by a ribozyme of RNA, which cleavage causes the cells to survive, and selecting those cells which survive.

Ribozymes which are obtained by the screening method herein can be used to selectively destroy RNA, such as that encoding human immunodeficiency virus (HIV) proteins, in vivo.

Also described herein is a method for generating a variety of oligonucleotides for screening by employing mixtures of nucleotide precursors in a DNA synthesizer.

BRIEF DESCRIPTION OF THE DRAWINGS

FIG. 4. Predicted secondary structure of the truncated ermC leader sequence. The ribosome binding site for the synthesis of methylase (shown as a boxed sequence) is in a single-stranded conformation that is accessible to ribosomes.

DETAILED DESCRIPTION OF THE INVENTION

Figure 1A:
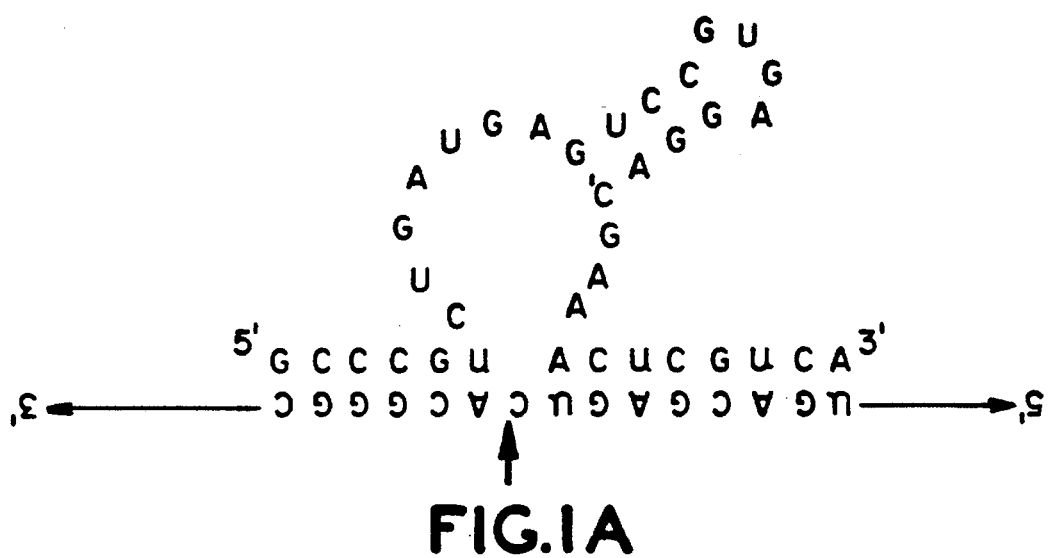
FIGS. 1A–1C. Ribozyme structure. (A). Haseloff-Gerlach ribozyme bound to its substrate. The 36-nucleotide-long RNA shown on the top is the ribozyme. The RNA on the bottom is the substrate strand. When the ribozyme is hybridized to the substrate and incubated with magnesium ions, it will catalyze the cleavage of the substrate at the site indicated by the arrow. (B). Catalytic domain of a Haseloff-Gerlach ribozyme. Invariant sequences (contained within the boxed region) are required for the cleavage of the substrate strand. (C). Complementary sequences of a Haseloff-Gerlach ribozyme. These variable sequences (shown as boxed regions) are chosen to be complementary to a preselected sequence in the substrate strand.

Using the method herein ribozymes are screened by culturing cells whose survival is dependent upon cleavage of RNA by a ribozyme within the cell. Cleavage by the ribozyme allows the cells to survive. The surviving cells are selected and contain the most effective ribozymes. The ribozymes obtained are more effective than those of the prior art. They are to be used, for example, to prevent viral replication in cells by cleaving the RNA required for the formation of the virus' constituent proteins.

This screening method can be utilized where the ribozyme to be screened cleaves any type of RNA which, when cleaved, permits the cell to survive. In one embodiment, the RNA is messenger RNA coding for a polypeptide, which when expressed causes the cells to survive in the media used to culture the cells. The cleavage by the ribozyme can, for example, allow translation of the polypeptide by altering the secondary structure of the messenger RNA. The alteration in secondary structure may free a ribosomal binding site which allows translation to thereafter take place.

In a most preferred embodiment the method is used for screening mutant ribozymes of the Haseloff-Gerlach type. In this embodiment cells are cultured whose survival is dependent upon cleavage by the ribozymes at a sequence inserted in a hairpin loop of the ermC leader in ermC messenger RNA. The cleavage causes a change in structure of the ermC messenger RNA and frees a ribosome binding site to allow synthesis of methylase, thereby permitting the cell to survive in media containing an MLS antibiotic. Cells which survive are selected.

The screening method can also include the formation of a library of ribozyme clones by creating a large number of vectors encoding ribozymes having different sequences which are to be screened, and transforming cells with the vectors. A strategy for constructing a library of mutant ribozymes which are likely to be effective is described herein.

As stated above, the catalytic domain of a more effective ribozyme to be obtained by using the screening technique disclosed herein can be related to the sequence in the Haseloff-Gerlach design. The number of possible sequences to test becomes enormous when multiple nucleotide substitutions are envisioned. An extensive library of ribozymes can be synthesized, however, each possessing a different sequence in its catalytic domain, but all possessing the same complementary sequences in their flanking segments. The method for creating this library is made possible because artificial ribozymes can be transcribed from synthetic DNA templates. During the synthesis of the template DNA for the ribozyme, nucleotide substitutions can be introduced at random at a relatively low frequency, into those positions in the sequence that specify the catalytic domain of the ribozyme. The RNAs transcribed from these DNA templates consist of a diverse collection of mutant ribozymes.

In order to identify the most efficient ribozymes in this mixture, a cell, for example a bacterial cell or a eukaryotic cell such as yeast, can be transformed and made to express the ribozyme. The survival of the cell is made dependent upon effective cleavage by the ribozyme of RNA in the cell. For example, DNA templates of ribozymes to be screened can be cloned into plasmids and introduced into a specially modified strain of Bacillus subtilis. These bacteria can be grown under conditions in which their survival in the presence of an antibiotic will depend on the efficient functioning of the ribozyme encoded in the plasmid. By examining plasmids from the few cells that are able to survive, mutant ribozymes can be identified that function efficiently under physiological conditions. Plasmids from these selected clones are isolated and their nucleotide sequences are determined in order to identify those nucleotide substitutions that are present in the most efficient ribozymes.

The ribozyme sequences selected from a first round of mutagenesis can then be used as the "wild-type" in a second round of mutagenesis and selection. In other words, a second set of ribozymes can be made for screening based on the sequence of a ribozyme or ribozymes found to be effective in the first round of screening. By repeating this process a number of times, natural evolution is mimicked, and the ribozyme sequence can be gradually refined until it is optimally suited for cleavage in trans.

If desired, the ribozymes obtained by the screening technique can be further tested for their ability to cleave target RNA, for example, HIV-1 mRNA, and their ability to block expression of the target RNA in human cells, such as human lymphocytes.

In a preferred embodiment, the efficiency of different mutant ribozymes can be tested by seeing whether a cell in which each ribozyme is expressed can grow in the presence of one of the macrolide-lincosamide-streptogramin B (MLS) group of antibiotics, preferably tylosin. Survival of each clone depends on the ability of its expressed ribozyme to efficiently cleave the highly structured leader sequence of ermC messenger RNA. The ermC gene, which is constitutively transcribed (Shivakumar et al., 1980), encodes a methylase (Shivakumar & Dubnau, 1981) whose activity confers resistance to the MLS antibiotics (Weisblum et al., 1979). However, the ermC methylase usually cannot be produced in sufficient quantity to confer resistance to the antibiotic because the AUG codon required for the initiation of methylase synthesis is sequestered in a secondary structure formed by the leader sequence of the ermC mRNA (Gryczan et al., 1980). Under natural conditions, resistance occurs in the presence of subinhibitory concentrations of another macrolide antibiotic, erythromycin, which initiates a sequence of events that leads to a structural reorganization of the ermC leader sequence that exposes the AUG initiation codon, resulting in the synthesis of the methylase (Gryczan et al., 1980).

Instead of growing bacteria in the presence of erythromycin, however, bacteria can be induced to synthesize ribozymes that are designed to cleave the ermC leader. Cleavage leads to a structural reorganization of the mRNA that is similar to the reorganization that occurs when erythromycin is present at low concentration. Preferably, ribozyme synthesis is under the control of an inducer, and the concentration of the inducer can be adjusted so that only a few molecules of ribozyme are synthesized. Only those clones expressing the most efficient mutant ribozymes grow in the presence of the MLS antibiotic.

The ermC gene can be expressed in various bacteria. *B. subtilis* can be used as the host cell, but appropriate modifications will be apparent to one skilled in the art to adapt the methodology described herein to other bacteria.

Similarly, the method of the invention may be applied in host cells containing messenger RNAs other than ermC wherein the messenger RNA rearranges, upon cleavage by a ribozyme, to allow expression of a polypeptide which allows the cell to survive. It has been shown that cleavage of RNA results in structural rearrangements (Kramer & Mills, 1981), and neighboring intrastrand complements that are predicted by a computer program to form stable secondary structures (Zuker and Stiegler, 1981) almost always form these structures (Jaeger et al., 1989). Thus, one skilled in the art can determine other messenger RNAs which can be cleaved in order to allow cell survival. The messenger RNA may encode, for example, a polypeptide which endows the cell with resistance to a different antibiotic, or which allows the cell to utilize a particular nutrient in order to survive. For example, expression of the messenger RNA coding for chloramphenicol resistance is regulated in a manner similar to that of ermC messenger RNA. Using the method described herein, bacteria which expressed only the most efficient ribozymes would survive in chloramphenicol-containing media because of resistance due to efficient cleavage of target messenger RNA.

An alternative target messenger RNA is one encoding a toxic peptide. Toxic peptides are well known in the art and include antibacterial peptides as well as peptides which are toxic to yeast or other eukaryotic cells. Messenger RNA encoding the toxic peptide can be placed under the control of an inducible regulator. When the ribozymes to be screened and the messenger RNA encoding the toxic peptide are expressed, under appropriate concentrations of inducer, then only cells containing the most effective ribozymes will survive.

The screening method may also be applied where the ribozyme to be screened cleaves RNA which is not messenger RNA, but which is otherwise responsible for the survival of the cell. For example, the copy number of a plasmid encoding antibiotic resistance can be controlled by RNA expressed in a cell, possibly expressed by a second plasmid. Cleavage of the RNA by a ribozyme leads to increased copy number and therefore increased antibiotic resistance. In one known system RNA species I is specified by a first plasmid and controls the copy number of a second plasmid which encodes antibiotic resistance (Tomizawa and Itoh, 1981). Ribozymes can be screened for efficient cleavage of RNA I, which cleavage increases the copy number of the plasmid encoding antibiotic resistance and allows the cell to survive in antibiotic containing media.

The structure and function of the ermC translational attenuator used in the preferred embodiment are now described.

Figure 2:
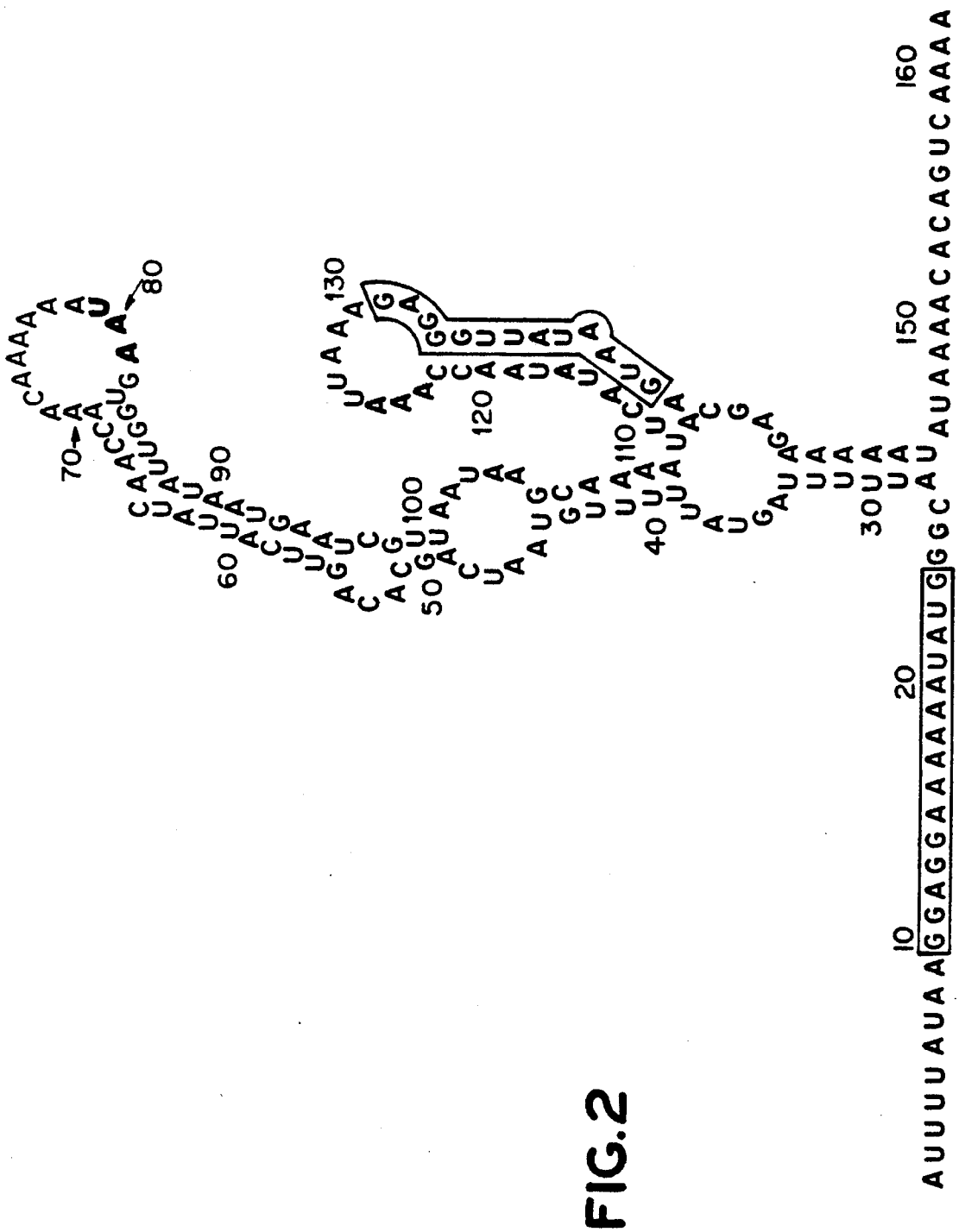
FIG. 2. Predicted secondary structure of the ermC leader sequence. Two potential ribosome binding sites are present (shown as boxed sequences). Each is associated with an AUG initiation codon. The UAA codon that terminates the first open reading frame is shown in bold letters. The second open reading frame, which encodes the methylase responsible for resistance to the MLS antibiotics, cannot be translated because its AUG initiation codon is in a double-stranded region, where it is not accessible to ribosomes.

Bacteria containing the ermC gene can resist all members of the macrolide-lincosamide-streptogramin B (MLS) group of antibiotics (including tylosin) when they are grown in the presence of erythromycin (Weisblum et al., 1971). The MLS antibiotics inhibit protein synthesis by binding to the 50S ribosomal subunit. The methylase specified by the ermC gene modifies a particular adenosine residue in 23S ribosomal RNA (Lai et al., 1973), preventing the binding of MLS antibiotics to the ribosome (Shivakumar et al., 1980). FIG. 2 shows the leader sequence of the ermC transcript folded into the secondary structures that a computer program (Zuker and Stiegler, 1981; Zuker, 1989) predicts are most stable. There are two ribosome binding sites (Shine & Dalgarno, 1974) in the sequence. The first ribosome binding site is in front of an open reading frame encoding a 19 amino acid leader peptide. Its AUG initiation codon is in a single-stranded conformation. The second ribosome binding site is in front of an open reading frame encoding the 244 amino acid ermC methylase, but its AUG initiation codon is sequestered in a double-stranded region of the leader. Nuclease digestion experiments and ribosome protection studies confirm that only the first binding site is available to ribosomes (Narayanan & Dubnau, 1985).

Figure 3A:
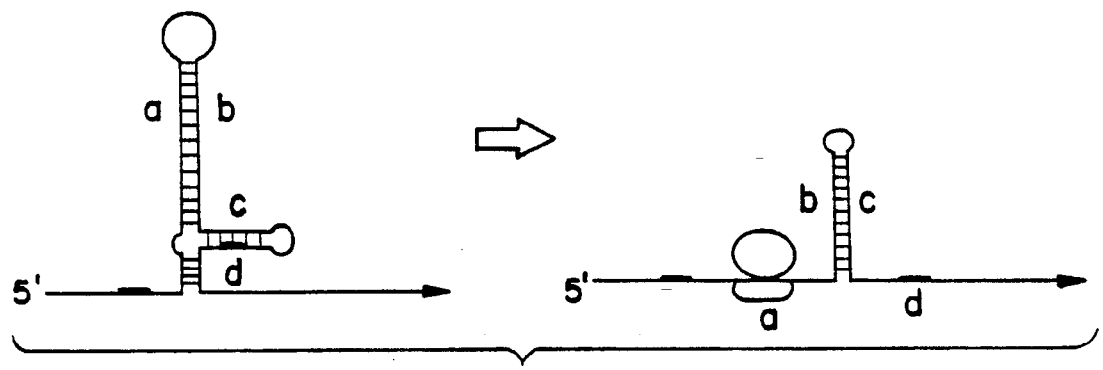
FIGS. 3A–3B. Structural reorganization of the ermC leader. (A). Reorganization by erythromycin induction. The panel on the left shows a schematic representation of the secondary structures formed by the ermC leader. The two ribosome binding sites are indicated by heavy lines. The methylase gene cannot be translated because its ribosome binding site is sequestered within the structure formed by regions c and d. The panel on the right shows a ribosome (to which erythromycin is bound) stalled in region a, resulting in the release of region b. Since the alternative structure that could be formed by regions b and c is more stable than the structure formed by regions c and d, a structural reorganization occurs that releases region d, freeing the ribosome binding site for the synthesis of methylase. (B). Reorganization by ribozyme cleavage. The panel on the left shows a schematic representation of the ermC leader with a ribozyme bound to the hairpin loop of the structure formed by regions a and b. Cleavage of this hairpin loop by the ribozyme truncates the leader sequence and results in the release of region b. Since the alternative structure that could be formed by regions b and c is more stable than the structure formed by regions c and d, a structural reorganization occurs that releases region d, freeing the ribosome binding site for the synthesis of methylase.

The function of this translational attenuator has been extensively studied by Dubnau and his colleagues (Dubnau, 1984), and is summarized below. In the absence of an MLS antibiotic, ribosomes bind to the first ribosome binding site and sweep through the leader, synthesizing many copies of the leader peptide. The methylase gene, on the other hand, is not translated because its initiation codon is not accessible to ribosomes. The rapid passage of ribosomes along the first open reading frame has no appreciable effect on the availability of the AUG codon at the beginning of the methylase gene. In the presence of most MLS antibiotics, the synthesis of proteins is halted after only one or two amino acids have been incorporated (Mao & Robishaw, 1971). Consequently, ribosomes that initiate synthesis of the leader peptide halt almost immediately after synthesis begins. In the presence of erythromycin, on the other hand, longer peptides are synthesized before translation is halted (Mao & Robishaw, 1972). Ribosomes that are bound to erythromycin and initiate the synthesis of the leader do not come to a halt until about nine amino acids have been incorporated (Mayford & Weisblum, 1989a, Mayford & Weisblum, 1989b). FIG. 3A illustrates how the resulting presence of a stalled ribosome in the leader sequence disrupts the secondary structure of the leader, resulting in a structural reorganization that places the AUG initiation codon for the methylase in a single-stranded conformation (Mayford & Weisblum, 1989b). At any given instant some ribosomes are not bound to an MLS antibiotic (Dubnau, 1984). Ribosomes that are not bound to the antibiotic are then able to synthesize the methylass, which goes on to modify ribosomal RNA, enabling the bacterium to survive in the presence of any MLS antibiotic.

Figure 3B:
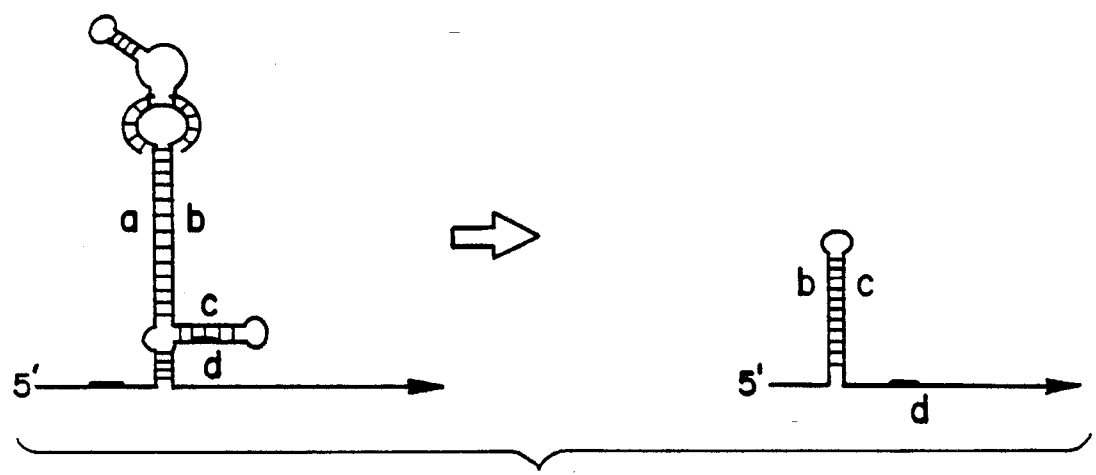
Figure 4:
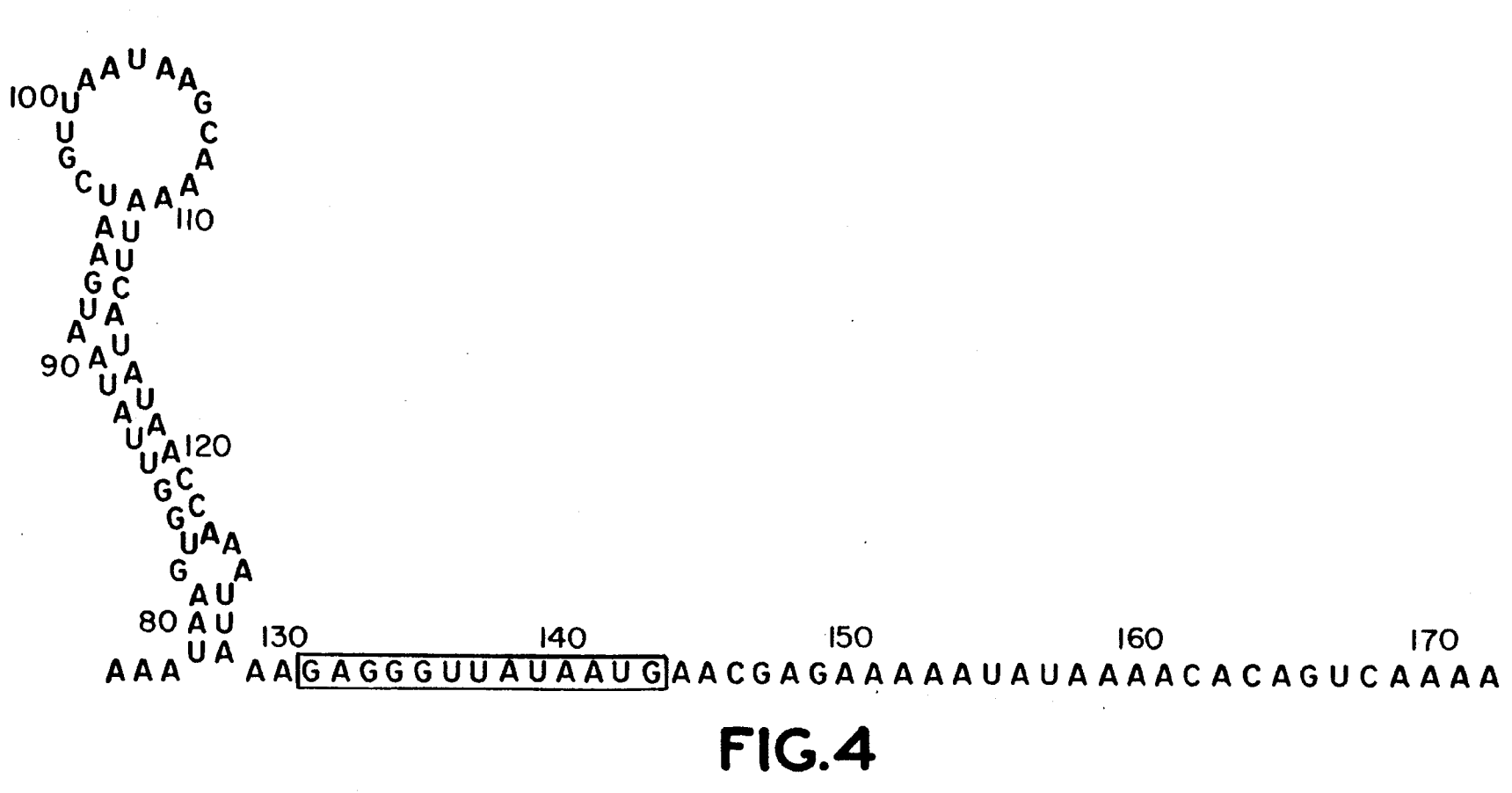

Ribozymes can cleave the ermC leader sequence. The resulting truncated ermC mRNA undergoes the same structural reorganization that occurs when a ribosome bound to erythromycin stalls while synthesizing the leader peptide. The cleavage fragments are forced apart as tylosin-free ribosomes sweep through the leader sequence. After dissociation of the fragments, the truncated ermC mRNA undergoes a structural reorganization that exposes the AUG initiation codon, permitting the synthesis of methylass by tylosin-free ribosomes. FIG. 3B illustrates this, and FIG. 4 shows the predicted secondary structure (Zuker, 1989; Zuker and Stiegler, 1981) of the truncated leader after reorganization occurs.

In a preferred embodiment for screening ribozymes, B. subtilis clones containing the ermC gene are grown on agar plates in the presence of tylosin, but in the absence of erythromycin. Normally, they all fail to form colonies. However, each clone is transformed to express a different mutant ribozyme that is designed to cleave the ermC leader. If the mutant ribozyme in a given clone functions efficiently in vivo, then a sufficient number of ermC transcripts are cleaved (and undergo the structural reorganization that allows the methylass to be synthesized) for the cells to resist the tylosin. The number of ribozyme molecules synthesized per cell is under the control of an inducer and is preferably kept at a very low level. Therefore only those clones possessing an extremely efficient mutant ribozyme survive. An examination of the sequences encoding the catalytic domain of the ribozymes in the selected clones identifies the advantageous mutations.

There are a number of alternate experimental routes that can be taken to select an efficient ribozyme. For example, a natural target sequence can be substituted for part of the ermC leader sequence. In other words, if the cleavage site of interest is contained in an HIV-1 target, then an HIV-1 sequence which includes the cleavage site can be substituted for the part of the ermC leader sequence which is to be cleaved. This substitution could be made, for example, in the hairpin loop of the ermC leader in place of nucleotides 70 through 82, as shown in FIG. 2. A mutant ribozyme can therefore be selected which will possess a catalytic domain that is already "fine-tuned" for the cleavage of the natural target sequence.

The selection method disclosed herein can be applied to ribozymes other than the Haseloff-Gerlach type. Recently, for example, another short ribozyme sequence has been identified (Hampel & Tritz, 1989) that forms a unique "hairpin" catalytic domain (Hampel et al., 1990) and is active under physiological conditions. As improved types of ribozymes become available they can be screened using this method to determine the particular sequences which are most catalytic.

Furthermore, although Haseloff-Gerlach ribozymes are described herein which have a catalytic sequence of 22 nucleotides, ribozymes which are variations on this conventional Haseloff-Gerlach design can be screened as well. For example, while nucleotide substitutions in the 22 nucleotide domain may be screened, insertions, additions, and deletions which change the number of nucleotides of the ribozyme can also be screened for effectiveness. It is anticipated that these ribozymes may have different structures than that shown in FIG. 1. Similarly, although 12–16 nucleotides are typically incorporated in the Haseloff-Gerlach design which are complementary to the target strand, ribozymes can be constructed for screening which have fewer or more of the complementary nucleotides than this number. A sufficient number of nucleotides, however, should be incorporated to make the ribozyme highly specific for the target.

The screening method can be used to determine ribozyme sequences most effective at cleaving any desired target sequence. In choosing the complementary sequences of the ribozyme, however, it should be kept in mind that not all potential target sites of the ribozymes to be screened are equally susceptible to attack. There are several considerations in choosing a target sequence. Of primary importance in designing a ribozyme to cleave viral RNA is the conservation of the chosen sequence among different isolates of the virus. For example, in HIV-NL43 genomic RNA, GUC occurs 46 times. Among characterized isolates of HIV-1 (listed in the Human Retroviruses and AIDS database), GUC is conserved at only 35 of these 46 positions; and flanking sequences (eight nucleotides in length) are conserved at only 18 of the sites. When the comparison is extended to African HIV-1 isolates, only seven sites fulfill the requirements. Another important consideration in selecting a target viral RNA is that it be located in a gene whose function or product is essential to the reproduction or infectivity of the virus. For example, the tat gene would be a good target because its gene product is a positive regulator of viral expression. The target should also occur in a region of RNA that is physically accessible to the ribozyme. In vitro studies have shown that the structure of the substrate RNA can be a major determinant of catalytic efficiency for Haseloff-Gerlach ribozymes (Fedor & Uhlenbeck, 1990). A computer program (Zuker, 1989; Zuker and Steigler, 1981) aids in predicting which secondary structures are most likely to occur.

While GUC is the best characterized cleavage site of the Haseloff-Gerlach ribozymes, GUU and GUA may, however, also serve as cleavage sites. Any cleavage site of a ribozyme to be tested, however, can be used in the target sequence, either that which the Haseloff-Gerlach ribozymes cleave, or sites which other ribozymes cleave. The site may either occur naturally in the sequence, or the target sequence may be adapted to contain the target site. In the ermC example described herein a GUC site is inserted in the target sequence. Where a natural sequence of, for a example, a virus, is spliced into the ermC gene, or other gene used, the viral sequence will normally already contain the cleavage site.

Following isolation of the effective ribozyme according to the method of the invention, follow up tests can, of course, be performed to see whether ribozyme-containing sequences that are complementary to a chosen target can cleave the target RNA in vitro. A further follow up test can be performed to determine the suitability of the target site by constructing a ribozyme to cleave it, and then observing the biological consequences of expression of the ribozyme in human cells challenged with the agent being treated. For example, once an effective ribozyme has been found according to our screening method which cleaves HIV-1 RNA, human lymphocytes can be transfected with a vector from which is expressed the ribozyme and can then be challenged with HIV-1 virus. An assay of HIV-1 infectivity can measure the effectiveness of the ribozyme in preventing HIV infection of the human cells. Such tests, while not involved with the practice of the invention, may nevertheless be useful follow-ups.

Following are examples which illustrate the invention. These examples should not be construed to limit the coverage of the claims which follow.

EXAMPLE 1

In this example we demonstrated the ability of Haseloff-Gerlach ribozymes, which were not screened according to the method of the invention, to cleave MDV-1 mRNA and HIV-1 integrase RNA.

Figure 5:
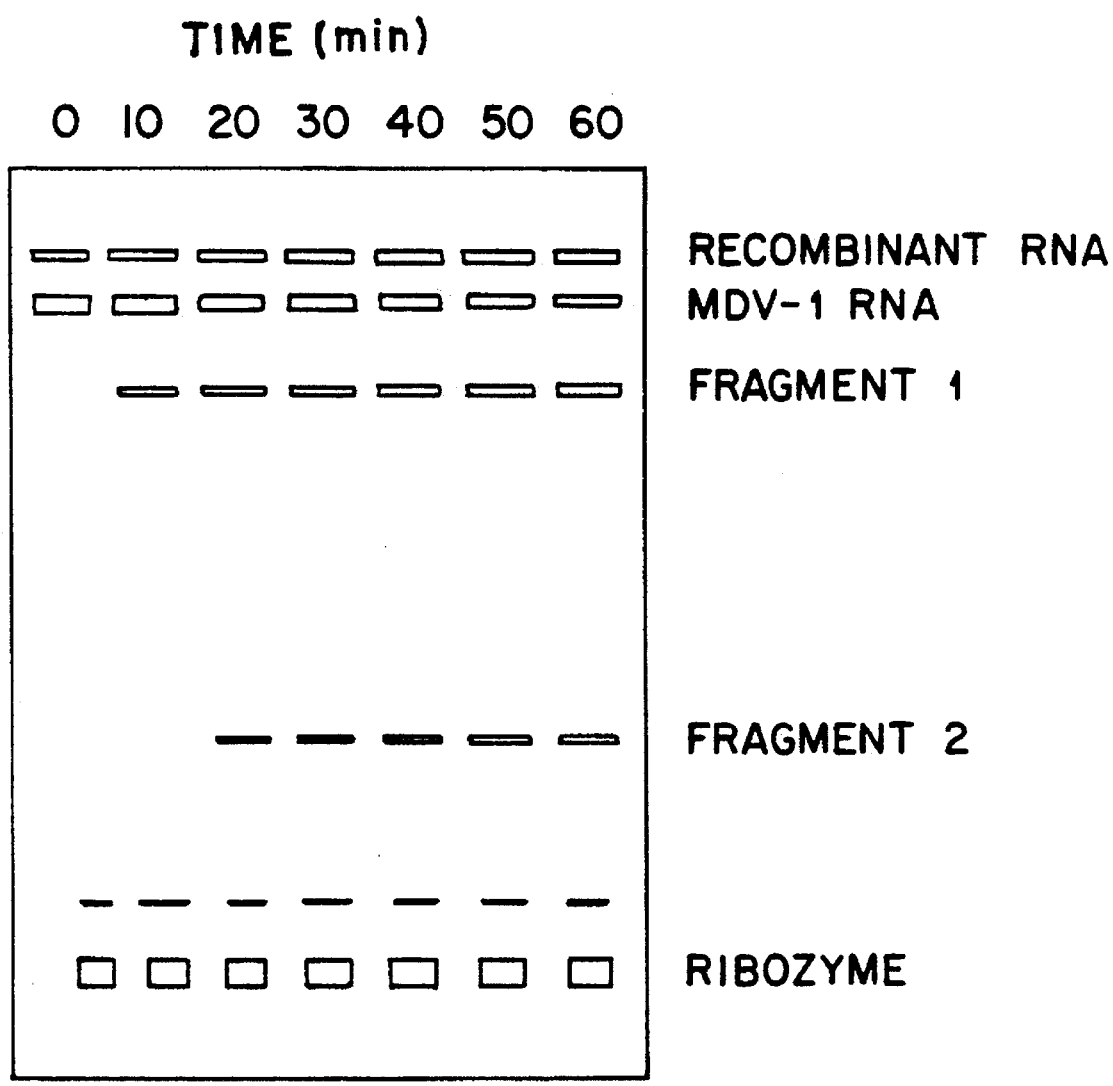
FIG. 5. Specific cleavage of an RNA by a ribozyme. An equimolar mixture of MDV-1 RNA and recombinant RNA was mixed with a 10-fold molar excess of a ribozyme designed to cleave the MDV-1 RNA. The recombinant RNA was a modified MDV-1 RNA that contained an additional sequence inserted within the ribozyme binding site. This mixture was incubated at 50 degrees Celsius in the presence of 20 mM magnesium chloride and 50 mM Tris-HCl (pH 8). Samples were taken at 10 minute intervals and were analyzed by electrophoresis through an 8% polyacrylamide gel containing 7M urea. The amount of ribozyme and the amount of recombinant RNA remained the same throughout the course of the reaction. The disappearance of MDV-1 RNA was accompanied by the appearance of MDV-1 RNA fragments of the expected size.

We constructed and tested a ribozyme that was designed to cleave MDV-1 RNA, which is a well-characterized template for Q-beta replicase (Kacian et al., 1972, Mills et al., 1973). The time-course of cleavage of MDV-1 RNA in vitro by this ribozyme is shown in FIG. 5. The incubation mixture included (as an internal control) a related recombinant RNA (Miele et al., 1983) which could not be cleaved because its ribozyme binding site was interrupted by the presence of an inserted heterologous sequence. Although the ribozyme cleaved its intended target (and did not cleave the control), the results demonstrated the relative inefficiency of the Haseloff-Gerlach design.

We prepared two Haseloff-Gerlach ribozymes, each designed to cleave the integrase gene of HIV-1 RNA at a position corresponding to the GUC at nucleotides 4669–4671 of the hybrid HIV-1 clone, HIV-NL43 (Adachi et al., 1986). The first ribozyme ("ribozyme alpha") was transcribed from a synthetic, single-stranded DNA template by incubation in vitro with bacteriophage T7 RNA polymerase (Milligan et al., 1987). Its sequence is shown below. Capital letters indicate the nucleotides that are complementary to the HIV-1 target sequence:

5'-g-CUACUACUCCUU-cugaugaguccgugaggacgaa-ACU-
      UUGGGGA-3'

The second ribozyme ("ribozyme beta") was transcribed from a recombinant plasmid, both in vitro (Melton et al., 1984) and in vivo. This plasmid contained the sequence encoding the ribozyme, embedded between a promoter for T7 RNA polymerase and a T7 transcription terminator. The plasmid was introduced into E. coli cells that contained a chromosomal copy of the T7 RNA polymerase gene from which T7 RNA polymerase could be inducibly expressed. The presence of the terminator in the plasmid ensures that the transcripts are homogeneous. Moreover, the presence of the terminator sequence at the 3' end of the transcripts provides protection from cellular exonucleases. The sequence of the second ribozyme is shown below:

5'-g-CUACUACUCCUU-cugaugaguccgugaggacgaa-ACU-
      UUGGGGCA-cauaaccccuugggggccucuaaacgggu-
      cuugaggguuuuuug-3'

Figure 6:
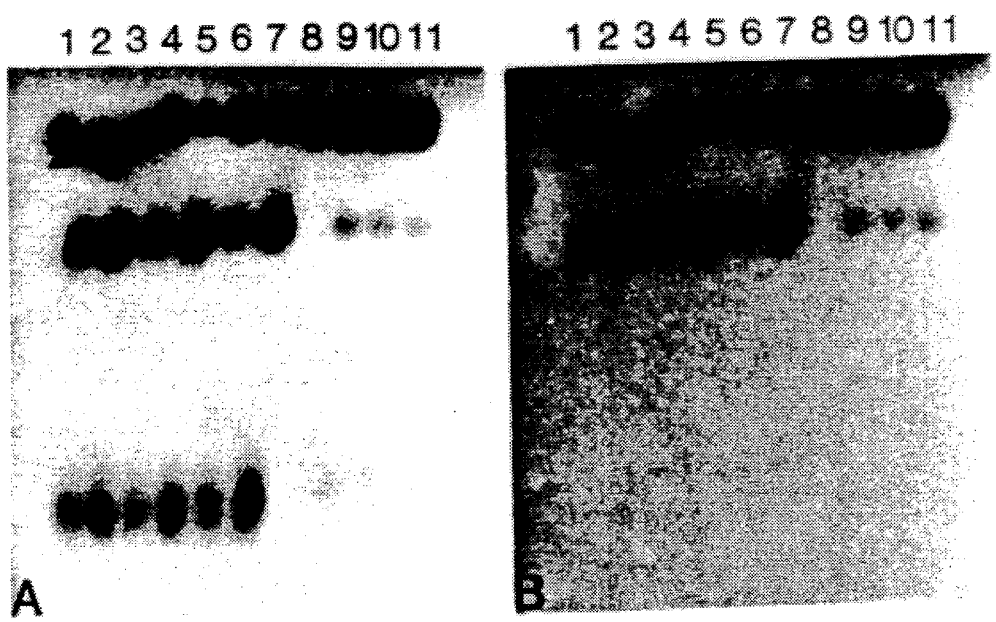
FIGS. 6A–6B. Cleavage of HIV-1 RNA in vitro. (A). Target RNA was incubated with ribozymes at 50 degrees Celsius, then analyzed by electrophoresis and visualized by hybridization with a probe for the HIV-1 integrase gene. Lane 1: no ribozyme, 60 min. Lane 2: ribozyme alpha, 30 min. Lane 3: ribozyme alpha, 60 min. Lane 4: ribozyme beta (synthesized in vitro), 30 min. Lane 5: ribozyme beta (synthesized in vitro), 60 min. Lane 6: ribozyme beta (synthesized in vivo), 30 min. Lane 7: ribozyme beta (synthesized in vivo), 60 min. Lane 8: mutant ribozyme beta with a deleted catalytic domain (synthesized in vivo), 60 min. Lanes 9, 10, and 11: repeat of reactions analyzed in lanes 2, 4, and 6, respectively, except that incubation was at 37 degrees Celsius. (B). Analysis of the incubation products by hybridization with a probe for the E. coli trpE gene.

Both ribozymes were studied in vitro. FIG. 6 shows a single experiment that illustrates the results. Each of the 11 reaction tubes contained "target RNA" which was total cellular RNA isolated from E. coli cells that express a trpE-HIV-1-integrase fusion protein. After incubation with a ribozyme, the RNA from each reaction was electrophoretically separated, transferred to a membrane, and hybridized with a radioactive probe for the HIV-1 integrase gene. The results showed that both ribozyme alpha and ribozyme beta cleave the target RNA into fragments of the expected size. It did not matter whether ribozyme beta was obtained by transcription in vitro or by the isolation of total cellular RNA from a bacterium in which its synthesis was induced. The results also demonstrated that ribozymes are able to function in the presence of unrelated cellular RNAs, and that the presence of a terminator sequence at the 3' end of the ribozyme does not prevent it from functioning. No cleavage occurred when ribozymes were omitted; and no cleavage occurred when a mutant ribozyme (lacking a catalytic domain) was present. The ribozymes were active in vitro at 50 degrees Celsius but were inactive at 37 degrees Celsius. However, experiments below demonstrated the ability of ribozymes to function in vivo at 37 degrees Celsius.

To confirm that cleavage occurred in the integrase portion of the target transcript (rather than in the trpE portion), the membranes were rehybridized with a probe for the E. coli trpE gene. The results showed that cleavage occurred within the HIV-1 integrase gene.

We also conducted a series of experiments to demonstrate the ability of ribozymes to cleave HIV-1 RNA in vivo. We prepared E. coli cells that contained a chromosomal copy of the T7 RNA polymerase gene under lac control and that also contained a plasmid in which the transcription of the HIV-1 integrase gene is regulated by a promoter for T7 RNA polymerase (strain A). We then prepared three additional E. coli strains by the introduction of a second (compatible) plasmid into strain A. The plasmids that were introduced into strain A contained an inserted gene under the control of a promoter for T7 RNA polymerase. In strain D, the inserted gene encoded ribozyme beta. In strain C, the inserted gene encoded a mutant ribozyme beta that lacked a catalytic domain. And in strain B, there was no inserted gene in the plasmid. The activity of the ribozymes transcribed from the inserted sequence in each strain was observed by transferring the bacteria to media containing an inducer of the lac operon. At various times after induction, growth was halted and the RNA in the cells was isolated, analyzed by electrophoresis, and visualized by hybridization with a radioactive probe for the HIV-1 integrase gene.

Figure 7:
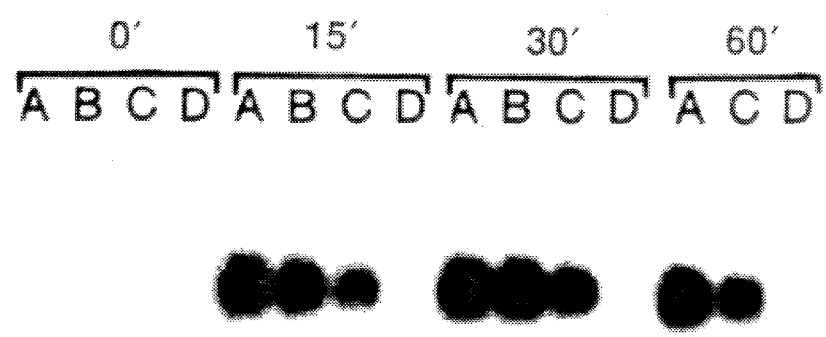
FIG. 7. Cleavage of HIV-1 RNA in vivo. Four different E. coli strains were induced to synthesize a transcript containing a HIV-1 target sequence and to simultaneously synthesize a second transcript, to see whether the second transcript could catalyze the cleavage of the target. At different times after induction, the RNA in the cells was isolated and analyzed by northern blotting to see whether the HIV-1 target was present, and if so, to see whether it was intact. The strains used and the time of induction are identified above each lane of the gel. The results demonstrate that if an intact ribozyme is present within the second transcript, then the HIV-1 RNA is completely destroyed.

The results (shown in FIG. 7) demonstrate that transcripts containing the HIV-1 target sequence are present after induction in cells that do not express a ribozyme (strains A and B). However, when ribozyme beta is expressed (strain D), the cleavage of the target RNA by the ribozyme apparently leads to the complete destruction of the cleaved transcripts by cellular endonucleases. A similar observation was made during the cleavage of HIV-1 RNA by ribozymes in cultured human cells (Sarver et al., 1990). The mutant ribozyme that lacked a catalytic domain (in strain C) apparently acted as a classic antisense RNA, modulating the expression of the target. Interestingly, ribozyme beta was active in vivo at 37 degrees Celsius, even though it was inactive in vitro at the same temperature. A ribozyme, therefore, apparently catalyzed the cleavage of an HIV-1 target at 37 degrees Celsius in vivo, leading to the complete destruction of the transcript.

EXAMPLE 2

This example demonstrates the preparation of a *B. subtilis* clone containing a single copy of a modified ermC gene.

ErmC normally occurs on a plasmid, pE194, which was isolated from Staphylococcus aureus (Iordanescu, 1976), and which can be transferred to *B. subtilis* by transformation (Weisblum et al., 1979). pE194 is deposited at the ATCC under accession number 68359.

A modified pE194 can be used in which a single basepair substitution is introduced into the ermC gene, so that it contains a unique EcoRI restriction site. Although this substitution results in a guanosine at position 109 of the ermC leader, it has no effect on ermC function or induction by erythromycin. In a further modification, a 3-basepair segment cleavable by the ribozymes to be tested can be inserted into the ermC gene. For example, a GUC sequence can be inserted between nucleotides 75 and 76 of the ermC leader (see FIG. 2). Since this insertion occurs in a hairpin loop and since it only adds a single in-phase codon to the leader sequence, it is unlikely to alter the function of the ermC gene. The insertion of a GUC sequence at this location allows the modified hairpin loop to serve as a substrate for cleavage by a Haseloff-Gerlach ribozyme.

Because a unique SstI restriction site occurs upstream of the ermC transcription initiation site (Narayanan & Dubnau, 1985), the insertion of the GUC, or other appropriate cleavage site, can be accomplished by replacing the SstI-EcoRI segment that encodes the beginning of the ermC leader with a synthetic DNA that is identical in all respects except that it contains the desired inserted basepairs.

In *B. subtilis*, pE194 is maintained at a copy number of approximately 10 at 37 degrees Celsius (Weisblum et al., 1979). It is desirable to reduce the amount of ermC mRNA that will be present in each cell to make it difficult for cells to survive unless they express an extremely efficient mutant ribozyme. Therefore, it is preferable to integrate a single copy of pE194, or other plasmid used which encodes ermC messenger RNA into the *B. subtilis* chromosome. An additional reason for integrating the particular plasmid pE194 into the chromosome is to prevent spontaneous loss of the plasmid, since the replication of pE194 is temperature-sensitive. The resulting clone can be tested to confirm that it is sensitive to tylosin in the absence of erythromycin, but resistant to tylosin in its presence. Integration of a single copy of pE194 containing the wild-type ermC gene can be accomplished by means known in the art (Hofemeister et al., 1983). In particular, the replication of pE194 is inhibited at elevated temperatures that do not interfere with the growth of *B. subtilis*. Selection for erythromycin-resistant organisms at elevated termperatures (circa 50 degrees Celsius) yields clones in which pE194 has been integrated into the *B. Subtilis* chromosome, and the erythromycin resistant determinant is therefore replicated as part of the chromosome. Integration occurs at essentially random positions on the chromosome. pE194 containing a native ermC sequence, or pE194 containing an inserted cleavage site, may be integrated in a single copy into the chromosome in this manner.

These strains, carrying pE194 insertions, can also be used as recipients for transformation or transduction with plasmids carrying a DNA segment of interest, together with a region of homology to the integrated pE194 element. This permits integration into the chromosome, with replacement of the resident pE194 sequence by the sequence on the plasmid, which may be an altered version of pE194 containing the cleavage site of interest. In this way, the segment of interest can be readily integrated at a known site on the *B. subtilis* chromosome.

EXAMPLE 3

This example demonstrates the preparation of a plasmid that can be induced to express a ribozyme to be screened for effectiveness. Use in the *B. subtilis* host is exemplified here but suitable plasmids may be made for expressing riboyzmes where other host cells are employed.

A recombinant plasmid, pLIQ-1, can be used in which transcription from a particular promoter is under the control of an *E. coli* lac operator, even though the plasmid is grown in *B. subtilis* (Yansura & Henner, 1984). Construction of this plasmid is described in U.S. Pat. No. 4,912,046, which is incorporated by reference into this application. This plasmid contains a hybrid promoter (called "spac"), that consists of a promoter from *B. subtilis* phage SPO-1 fused to an *E. coli* lac operator. The plasmid also contains an *E. coli* lac repressor gene under the control of a promoter and ribosome binding site that allows expression of the repressor in *B. subtilis*. The spac promoter is immediately upstream from a sequence that contains unique restriction sites for HindIII and XbaI. Consequently, the transcription of a sequence inserted between the HindIII and XbaI sites can be modulated in *B. subtilis* by altering the concentration of isopropyl-B-D-thiogalactoside (IPTG), which is an inducer of the *E. coli* lac operon.

A sequence is inserted downstream from the spac promoter that consists of two sections. The first section encodes a Haseloff-Gerlach ribozyme designed to cleave the modified leader sequence of the ermC transcript at the site of the GUC insertion. The second section contains the sequence of a transcription terminator. One transcription terminator which can be used, and is used here, is the major rho-independent transcription terminator of the comG gene of *B. subtilis* (Albano et al., 1989), the sequence of which is contained in the second oligonucleotide shown below. Each section can be prepared on commercially available DNA synthesizers. The sequence of the first oligonucleotide (encoding the ribozyme) is 5'-ggaa-GCTTATTT-ctgatgagtccgtgaggacgaa-ACTTTGTT-gtac-3'

Capital letters identify the sequences that encode the portions of the ribozyme that hybridize to the ermC leader. The 22 nucleotide catalytic domain of the ribozyme is encoded by the region between the capitalized sequences. A HindIII recognition sequence (AAGCTT) is close to the 5' end of the oligonucleotide. The sequence of the second oligonucleotide (containing the terminator) is 5'-ggtctag-AAAAAAAAGGTACCCGCTCGCTCTGGTAC-aa-caaagtttc-3'

Capital letters identify the region that is the complement of the sequence that will occur at the 3' end of terminated transcripts. An XbaI recognition sequence (TCTAGA) is close to the 5' end of the oligonucleotide. The last 15 nucleotides at the 3' end of each oligonucleotide are complementary to each other. Therefore, the two oligonucleotides will hybridize to each other and can be extended by incubation with the Klenow fragment of *E. coli* DNA polymerase, generating a double-stranded DNA segment encoding both a ribozyme and a transcription terminator. This segment is digested with HindIII and XbaI to generate "sticky" ends, and then inserted in place of the short HindIII-XbaI segment downstream from the spac promoter in pLIQ-1. The resulting recombinant plasmid is used to transform *B. subtilis* cells containing the modified chromosomal ermC gene described above. pLIQ-1 also contains a chloramphenicol resistance gene (Yansura & Henner, 1984), and transformants are selected by growth in the presence of chloramphenicol. Other resistance markers may, of course, be used.

Figure 8:
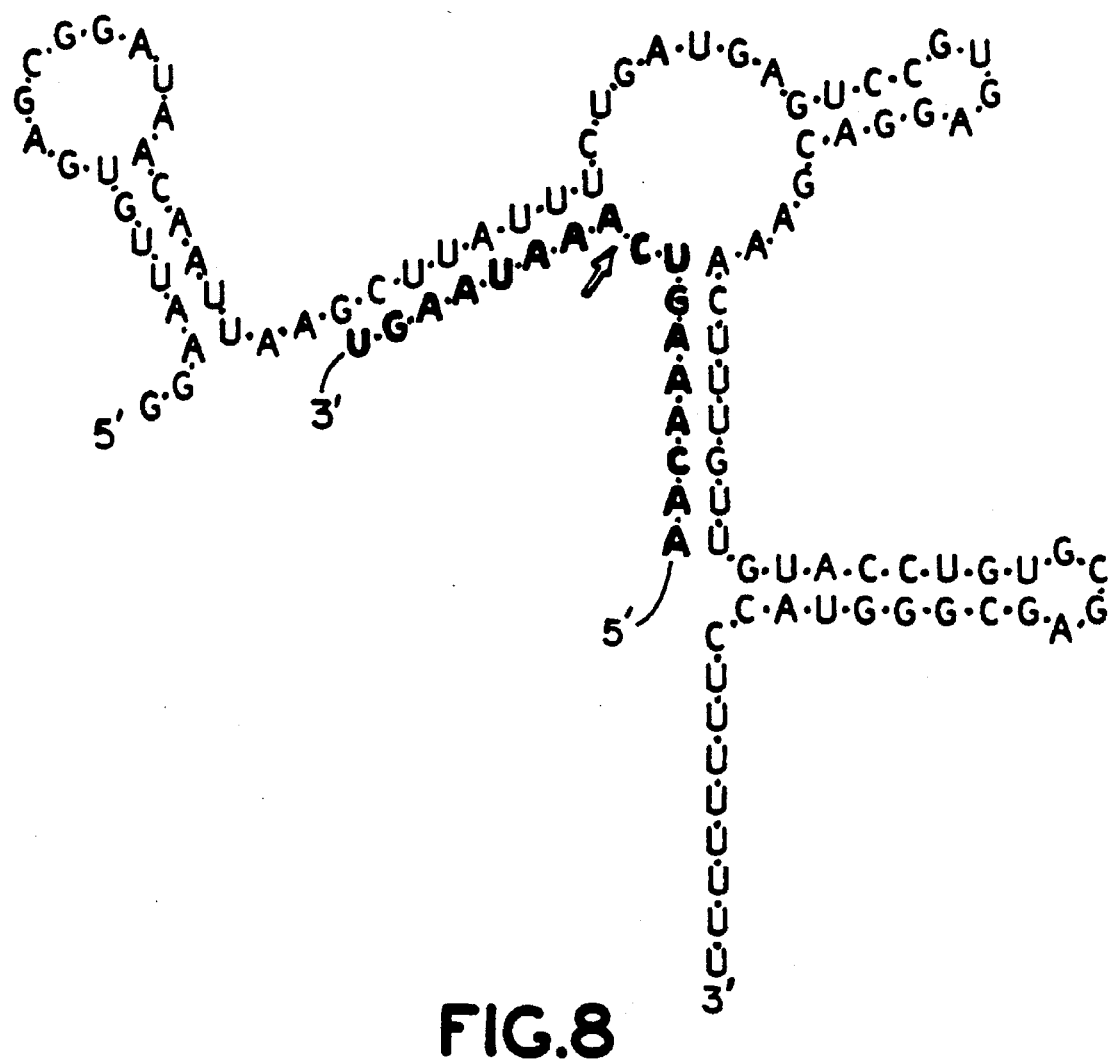
FIG. 8. Transcript containing a Haseloff-Gerlach ribozyme bound to a modified ermC leader. The 5' end of the transcript contains a secondary structure formed from the "palindromic" elements of the E. coli lac operator. The 3' end of the transcript contains a secondary structure that is characteristic of a rho-independent transcription terminator. The ribozyme is designed to catalyze the cleavage of the ermC leader (shown in bold letters) at the site indicated by the arrow.

When the selected clones are grown in the presence of IPTG, transcripts synthesized from the spac promoter consist of three sections: a 5' leader containing a copy of the *E. coli* lac operator, an ermC-specific Haseloff-Gerlach ribozyme, and a 3' tail containing the transcription terminator. FIG. 8 shows this transcript bound to the modified ermC leader. The arrow indicates the site where cleavage will occur. When deciding which terminator sequence to incorporate into the transcript, we used a computer program (Zuker, 1989; Zuker and Stiegler, 1981) to predict the secondary structures that are likely to form in the transcript. The program predicted that the comG terminator sequence is unlikely to interact with the sequence of the ribozyme. Furthermore, the program predicted that the sequences that must interact with the ermC leader for the ribozyme to function are likely to occur in a single-stranded conformation. Where ribozymes are designed to cleave targets contained in other sequences than the ermC leader, secondary structures may be similarly analyzed to select an appropriate terminator sequence, should a terminator sequence be included.

A northern blot procedure (Kornblum et al., 1988) can be used to confirm that the amount of ribozyme synthesized in transformed cells is dependent on the concentration of IPTG.

EXAMPLE 4

This example describes the preparation of a plasmid library containing mutant ribozyme sequences to be screened according to the method of the invention.

The automated synthesis of DNA occurs in a stepwise fashion, beginning at the 3' end of the desired oligonucleotide. When a new nucleotide is added to a growing oligonucleotide chain, the automated synthesizer selects an appropriate nucleotide precursor solution from the four solutions (one solution for each possible nucleotide) that are available. At any step of the synthesis, the substitution of a mixture of all four nucleotides in place of a single nucleotide will result in the incorporation of a mutant base at that location in some of the chains (Hutchison III et al., 1986). The proportion of oligonucleotides that will be mutant will depend on the relative amounts of "incorrect" nucleotide precursors present at each step. In this context, the terms "mutant nucleotides" and "incorrect nucleotides" refer to nucleotides which are different than those in the ribozyme whose sequence is being varied.

In one method for generating mutants, synthesis of the first oligonucleotide (encoding the ribozyme) proceeds until the first 12 nucleotides have been incorporated, forming a sequence which is complementary to the target sequence. At that point, all four of the precursor solutions are replaced with mixtures containing, for example, 85% of the "wild-type" nucleotide and 5% of each of the other three nucleotides. Synthesis of the oligonucleotide is then continued until the next 22 nucleotides (encoding the catalytic domain of the ribozyme) have been incorporated. Thus, in each of these 22 cycles of synthesis, 15% of the growing strands, at random, have incorporated one of the three "mutant" nucleotides. Synthesis is then halted, and the precursor mixtures are replaced with the original pure solutions. Synthesis is then continued until the remaining 12 nucleotides, which are complementary to the target sequence, have been incorporated. The product DNA therefore consists of a diverse collection of oligonucleotides encoding a variety of mutant ribozymes. These oligonucleotides are then hybridized to the second oligonucleotide, which encodes the transcription terminator, and extended and cloned into an appropriate plasmid, for example pLIQ-1 as described above. We estimate that a single oligonucleotide preparation can be used to construct at least 1 microgram of recombinant plasmids.

Since transformation of *B. subtilis* requires plasmid oligomers (Contente & Dubnau, 1979) and is therefore relatively inefficient, *E. coli* can be transformed with the recombinant plasmids, markedly increasing the number of transformants that can be obtained. Furthermore, if the DNA is transferred to the cells by electroporation, this should yield about a billion transformants per microgram of plasmid (Dower et al., 1988). The plasmids, markedly increasing the number of transformants that can be obtained. Furthermore, if the DNA is transferred to the cells by electroporation, this should yield about a billion transformants per microgram of plasmid (Dower et al., 1988). The main advantage of first introducing the plasmids into *E. coli* is that the proportion of oligomers in the plasmid population increases during bacterial growth (James et al., 1982). The transformed *E. coli* cells are grown on agar plates containing chloramphenicol, until they form nearly confluent bacterial lawns. The bacteria are then scraped off the plates and used to prepare plasmid DNA. The isolated plasmids are then transferred to *B. subtilis* by transformation. As a consequence of the preamplification in *E. coli*, approximately 10 million *B. subtilis* transformants should be obtained. Approximately 97% of these transformants encode a mutant ribozyme.

The number of different possible mutant sequences that are 22 nucleotides long, i.e. the length of the catalytic sequence which is to be varied, exceeds 17 trillion. If, for example, 10 million transformants are to be tested per experiment, a strategy should be employed to increase the chances of selecting a mutant ribozyme with enhanced activity. The number of different sequences n nucleotides long that contain exactly r mutations, $S_{n,r}$, is given by the formula:

$$S_{n,r}=[C_{n,r}][3^r]$$

where n equals 22, as is the case for the catalytic domain of ribozymes described in these examples, it is apparent that even with 10,000,000 transformants, only the different mutant strands that contain five or fewer nucleotide substitutions could be extensively explored.

| r | $S_{22,r}$ |
|---|---|
| 0 | 1 |
| 1 | 66 |
| 2 | 2,079 |
| 3 | 41,580 |
| 4 | 592,515 |
| 5 | 6,399,162 |
| 6 | 54,392,876 |
| 7 | 372,979,712 |
| 8 | 2,098,011,008 |

The number of transformants with sequences that are n nucleotides long and that contain exactly r mutations, $N_{n,r}$, that are expected to appear in a population containing 10,000,000 transformants, is given by the formula:

$$N_{n,r}=10,000,000[C_{n,r}][(3p)^r][(1-3p)^{(n-r)}]$$

where p is the frequency at which a particular mutant nucleotide is substituted for the wild-type nucleotide at a given position in the sequence. When we described the synthesis of the collection of mutant oligonucleotides above, p was set at 0.05. When n equals 22, as is the case for the catalytic domain of ribozymes described in these examples, the first eight values of $N_{n,r}$ are given in the table on the next page. It is clear from an examination of the table that if the substitution frequency, p is altered by changing the proportions of the nucleotides in the precursor mixtures, the way in which the selection experiment explores changes in the 22 nucleotides will be varied. Lower values of p will result in a thorough exploration of the different sequences that have only a few nucleotide substitutions. However, lower values of p will also result in only a relatively few sequences possessing the multiple substitutions that might confer increased ribozyme activity. Higher values of p, on the other hand, sacrifice a thorough exploration of minor changes for a greater representation of relatively complex mutants.

Our preferred strategy recognizes that all the possibilities cannot be explored directly. Instead, a relatively moderate value of p (0.05) is utilized to increase the probability of identifying advantageous alterations involving only a few mutations. Once these mutations have been identified, the synthesis of a collection of mutant sequences can be repeated, but starting with one or more of the advantageous sequences identified in the first collection, and using more stringent selection conditions (e.g. lower concentrations of IPTG). This strategy thus mimics the evolution of genes in nature. The selection process can be repeated a number of times. With each cycle of mutation and selection, small changes should improve the efficiency of the ribozyme. In this manner, a ribozyme is selected that is much more suited to cleaving a substrate under physiological conditions than the starting ribozyme whose sequence is varied. The ribozyme obtained is also much more efficient at catalyzing cleavage in trans than the natural hammerhead that evolved to catalyze cleavage in cis.

| | $N_{n,r}$ | | |
|---|---|---|---|
| r | p = .01 | p = .05 | P = .10 |
| 0 | 5,116,564 | 280,038 | 3,910 |
| 1 | 3,481,373 | 1,087,205 | 36,864 |
| 2 | 1,130,549 | 2,014,528 | 165,888 |
| 3 | 233,103 | 2,370,032 | 473,966 |
| 4 | 34,244 | 1,986,645 | 964,859 |
| 5 | 3,812 | 1,262,104 | 1,488,640 |
| 6 | 334 | 631,052 | 1,807,634 |
| 7 | 24 | 254,542 | 1,770,744 |
| 8 | 1 | 84,223 | 1,422,919 |

Figure 1B:
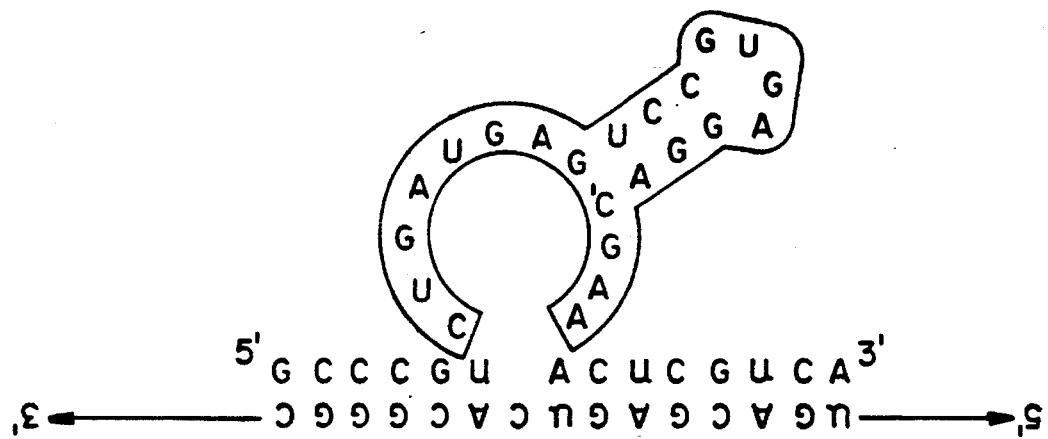
Figure 1C:
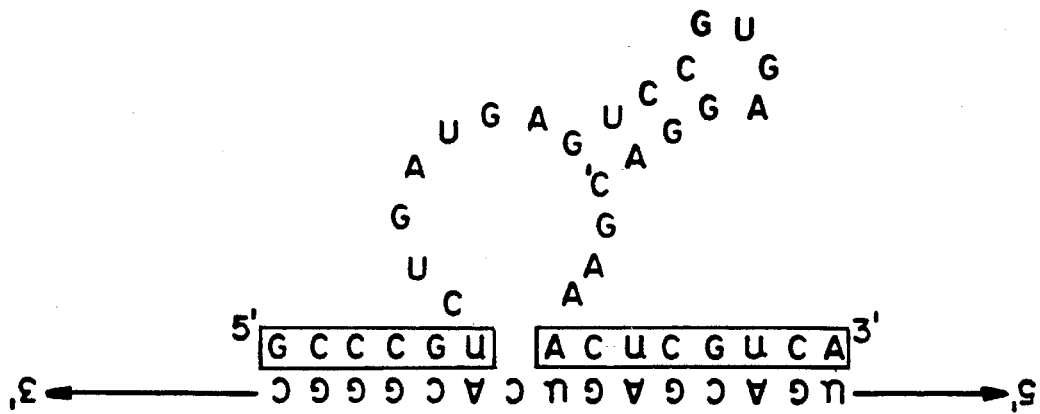

We have described introducing mutations into all 22 nucleotides of the catalytic domain, even though the only conserved sequences (Forster & Symons, 1987b) are those surrounding the hairpin structure (see FIG. 1B). We chose this route because the mechanism of catalysis is not understood, and the identity of the sequences that form this hairpin markedly influence the rate of cleavage (Heus et al., 1990). In another approach, however, a lesser number of nucleotides may be targeted for selection if it is believed those nucleotides are more influential in the ribozyme's catalytic action. For example, the ten unhybridized nucleotides shown in FIG. 1B "CUGAUGA . . . GAA" can be varied, and the others in the 22 nucleotide catalytic sequence kept the same, based on a presumption that these nucleotides are more responsible catalyzing the cleavage of the target RNA.

EXAMPLE 5

In this example, transformants are selected which express the most efficient mutant ribozymes.

The library of transformed B. subtilis clones is grown on agar containing 10 micrograms/ml tylosin and varying concentrations of IPTG (between 0 and 1,000 micrograms/ml). No colonies should grow in the absence of IPTG because not enough ribozymes are synthesized for the cells to be able to grow in the presence of tylosin. In the presence of IPTG, many more ribozymes are synthesized in each cell. However, most of the clones are still unable to grow because the ribozymes they synthesize are not sufficiently active in vivo. The clones that do survive contain a mutant ribozyme that is considerably more active than the wild-type.

As noted above, the antibiotic resistance is caused by the disassociation of the RNA fragments created when the ribozyme cleaves the ermC mRNA.

At lower IPTG concentrations, fewer molecules of ribozyme are transcribed. The IPTG concentration is determined at which only about 20 to 30 clones are able to survive. The clones that grow in this low IPTG concentration contain the most efficient ribozyme mutants. The fastest growing clones from this collection are isolated for further study. These clones are tested to confirm that they are sensitive to tylosin and that they are able to grow in tylosin if either IPTG or erythromycin is present. Active ribozyme mutants can be distinguished from constitutive mutants of ermC because the constitutive mutants are resistant to tylosin in the absence of inducer, while the ribozyme mutants are not.

Plasmid DNA from selected clones is isolated and the HindIII-XbaI fragment from each is sequenced to determine which nucleotide substitutions in the catalytic domain of the Haseloff-Gerlach ribozyme are responsible for increased activity in vivo.

REFERENCES

Adachi, A., Gendelman, H., Koenig, S., Folks, T., Willey, R., Rabson, A., & Martin, M. (1986). Production of acquired immunodeficiency syndrome-associated retrovirus in human and nonhuman cells transfected with an infectious molecular clone. J. Virol. 59, 284–291.

Albano, M., Breitling, R., & Dubnau, D. (1989). Nucleotide sequence and genetic organization of the Bacillus subtilis comG operon. J. Bacteriol. 171, 5386–5404.

Cameron, F., & Jennings, D. (1989). Specific gene supression by engineered ribozymes in monkey cells. Proc. Natl. Acad. Sci. USA 86, 9139–9143.

Contente, S., & Dubnau, D. (1979). Characterization of plasmid transformation in Bacillus subtilis: kinetic properties and the effect of DNA conformation. Mol. Gen. Genet. 167, 251–258.

Cotten, M., Schaffner, G., & Birnstiel, M. L. (1989). Ribozyme, antisense RNA, and antisense DNA inhibition of U7 small nuclear ribonucleoprotein-mediated histone pre-mRNA processing in vitro. Mol. Cell. Biol. 9, 4479–4487.

Dower, W. J., Miller, J. F., & Ragsdale, C. W. (1988). High efficiency transformation of E. coli by high voltage electroporation. Nucleic Acids Res. 16, 6127–6145.

Dubnau, D. (1984). Translational attenuation: the regulation of bacterial resistance to the macrolide-lincosamide-streptogramin B antibiotics. CRC Critical Rev. Biochem. 16, 103–132.

Fedor, M. J., & Uhlenbeck, O. C. (1990). Substrate sequence effects on hammerhead RNA catalytic efficiency. Proc. Natl. Acad. Sci. USA 87, 1668–1672.

Forster, A. C., & Symons, R. H. (1987a). Self-cleavage of plus and minus RNAs of a virusoid and a structural model for the active sites. Cell 49, 211–220.

Forster, A. C., & Symons, R. H. (1987b). Self-cleavage of virusoid RNA is performed by the proposed 55-nucleotide active site. Cell 50, 9–16.

Gryczan, T. J., Grandi, G., Hahn, J., Grandi, R., & Dubnau, D. (1980). Conformational alteration of mRNA structure and the posttranslational regulation of erythromycin-induced drug restance. Nucleic Acids Res. 8, 6081–6097.

Hampel, A., & Tritz, R. (1989). RNA catalytic properties of the minimum (–)sTRSV sequence. Biochemistry 28, 4929–4933.

Hampel, A., Tritz, R., Hicks, M., & Cruz, P. (1990). Hairpin catalytic RNA model: evidence for helices and sequence requirement for substrate RNA. Nucleic Acids Res. 18, 299–304.

Haseloff, J., & Gerlach, W. L. (1988). Simple RNA enzymes with new and highly specific endoribonuclease activities. Nature 334, 585–591.

Heus, H. A., Uhlenbeck, O. C., & Pardi, A. (1990). Sequence-dependent structural variations of hammerhead RNA enzymes. Nucleic Acids Res. 18, 1103–1108.

Hofemeister, J., Israeli-Reches, M., & Dubnau, D. (1983). Integration of plasmid pE194 at multiple sites on the Bacillus subtilis chromosome. Mol. Gen. Genet. 189, 58–68.

Hutchins, C. J., Rathjen, P. D., Forster, A. C., & Symons, R. H. (1986). Self-cleavage of plus and minus RNA transcripts of avacado sunblotch viroid. Nucleic Acids Res. 14, 3627–3640.

Hutchison III, C. A., Nordeen, S. K., Vogt, K., & Edgell, M. H. (1986). A complete library of point substitution mutations in the glucocorticoid response element of mouse mammary turmor virus. Proc. Natl. Acad. Sci. USA 83, 710–714.

Iordanescu, S. (1976). Three distinct plasmids originating in the same Staphylococcus aureus strain. Arch. Roum. Pathol. Exp. Microbiol. 35, 111–118.

Jaeger, J. A., Turner, D. H., & Zuker, M. (1989). Improved predictions of secondary structures for RNA. Proc. Natl. Acad. Sci. USA 86, 7706–7710.

James, A. A., Morrison, P. T., & Kolodner, R. (1982). Genetic recombination of bacterial plasmid DNA. Analysis of the effect of recombination-deficient mutations on plasmid recombination. J. Mol. Biol. 160, 411–430.

Kacian, D. L., Mills, D. R., Kramer, F. R., & Spiegelman, S. (1972). A replicating RNA molecule suitable for a detailed analysis of extracellular evolution and replication. Proc. Natl. Acad. Sci. USA 69, 3038–3042.

Koizumi, M., Iwai, S., & Ohtsuka, E. (1988). Cleavage of specific sites of RNA by designed ribozymes. FEBS Lett. 239, 285–288.

Kornblum, J., Projan, S. J., Moghazeh, S. L., & Novick, R. (1988). A rapid method to quantitate non-labeled RNA species in bacterial cells. Gene 63, 75–85.

Kramer, F. R., & Mills, D. R. (1981). Secondary structure formation during RNA synthesis. Nucleic Acids Res. 9, 5109–5124.

Kruger, K., Grabowski, P. J., Zaug, A. J., Sands, J., Gottschling, D. E., & Cech, T. R. (1982). Self-splicing RNA: autoexcision and autocyclization of the ribosomal RNA intervening sequence of Tetrahymena. Cell 31, 147–157.

Lai, C. J., Dahlberg, J. E., & Weisblum, B. (1973). Structure of an inducibly methylatable nucleotide sequence in 23S ribosomal ribonucleic acid from erythromycin-resistant Staphylococcus aureus. Biochemistry 12,457–460.

Mao, J. C. H., & Robishaw, E. E. (1971). Effects of macrolides on peptide-bond formation and translocation. Biochemistry 10, 2054–2061.

Mao, J. C. H., & Robishaw, E. E. (1972). Erythromycin, a peptidyltransferase effector. Biochemistry 11, 4864–4872.

Mayford, M., & Weisblum, B. (1989a). ErmC leader peptide. Amino acid sequence critical for induction by translational attenuation. J. Mol. Biol. 206, 69–79.

Mayford, M., & Weisblum, B. (1989b). Conformational alterations in the ermC transcript in vivo during induction. EMBO J. 8, 4307–4314.

Melton, D. A., Krieg, P. A., Rebagliati, M. R., Maniatis, T., Zinn, K., & Green, M. R. (1984). Efficient in vitro synthesis of biologically active RNA and RNA hybridization probes from plasmids containing a bacteriophage SP6 promoter. Nucleic Acids Res. 12, 7035–7056.

Miele, E. A., Mills, D. R., & Kramer, F. R. (1983). Autocatalytic replication of a recombinant RNA. J. Mol. Biol. 171, 281–295.

Milligan, J. F., Groebe, D. R., Witherall, G. W., & Uhlenbeck, O. C. (1987). Oligonucleotide synthesis using T7 RNA polymerase and synthetic DNA templates. Nucleic Acids Res. 15, 8783–8798.

Mills, D. R., Kramer, F. R., & Spiegelman, S. (1973). Complete nucleotide sequence of a replicating RNA molecule. Science 180, 916–927.

Narayanan, C. S., & Dubnau, D. (1985). Evidence for the translational attenuation model: ribosome-binding studies and structural analysis with an in vitro run-off transcript of ermC. Nucleic Acids Res. 13, 7307–7326.

Prody, G. A., Bakos, J. T., Buzayan, J. M., Schneider, I. R., & Bruening, G. (1986). Autolytic processing of dimeric plant virus satellite RNA. Science 231, 1577–1580.

Sarver, N., Cantin, E. M., Chang, P. S., Zaia, J. A., Ladne, P. A., Stephens, D. A., & Rossi, J. J. (1990). Ribozymes as potential anti-HIV-1 therapeutic agents. Science 247, 1222–1225.

Shine, J., & Dalgarno, L. (1974). The 3'-terminal sequence of *Escherichia coli* 16S ribosomal RNA: complementarity to nonsense triplets and ribosome binding sites. Proc. Natl. Acad. Sci. USA 1, 1342–1346.

Shivakumar, A. G., Hahn, J., Grandi, G., Kozlov, Y., & Dubnau, D. (1980). Posttranscriptional regulation of an erythromycin resistance protein specified by plasmid pE194. Proc. Natl. Acad. Sci. USA 77, 3903–3907.

Shivakumar, A. G., & Dubnau, D. (1981). Characterization of a plasmid-specified ribosome methylase associated with macrolide resistance. Nucleic Acids Res. 9, 2549–2562.

Tomizawa, J., & Itoh, T. (1981). Plasmid ColE1 incompatability determined by interaction of RNAI with primer transcript. Proc. Natl. Acad. Sci. USA 78, 6096–6100.

Uhlenbeck, O. C. (1987). A small catalytic oligoribonucleotide. Nature 328, 596–600.

Weisblum, B., Siddhikol, C., Lai, C. J., & Demohn, V. (1971). Erythromycin-inducible resistance in *Staphylococcus aureus*: requirements for induction. J. Bacteriol. 106, 835–847.

Weisblum, B., Graham, M. Y., Gryczan, T., & Dubnau, D. (1979). Plasmid copy number control: isolation and characterization of high-copy-number mutants of plasmid pE194. J. Bacteriol. 137, 635–643.

Yansura, D. G., & Henner, D. J. (1984). Use of the *Escherichia coli* lac repressor and operator to control gene expression in Bacillus subtilis. Proc. Natl. Acad. Sci. USA 81, 439–443.

Zuker, M. (1989). On finding all suboptimal foldings of an RNA molecule. Science 244, 48–52.

Zuker, M. and Stiegler, P. (1981). Optimal computer folding of large RNA sequences using thermodynamics and auxiliary information. Nucleic Acids Res. 9, 133–148.

We claim:

1. A method for screening hammerhead or hairpin ribozymes for effectiveness in cleaving RNA comprising
   a) creating a plurality of vectors encoding ribozymes specific for a single target RNA sequence and having differing catalytic domain sequences, which ribozymes are to be screened for effectiveness in cleaving RNA containing the target RNA sequence;
   b) providing bacterial cells that possess RNA containing the target RNA sequence and that, when the RNA is cleaved in sufficient quantity by one of the ribozymes, survive in a preselected culture medium;
   c) transforming the cells with the vectors;
   d) culturing the cells in the preselected culture medium under conditions wherein the ribozymes are expressed; and
   e) selecting cells which survive.

2. The method of claim 1 wherein the cells are bacteria.

3. The method of claim 2 wherein the bacteria are *B. subtilis* bacteria.

4. A method for screening hammerhead or hairpin ribozymes for effectiveness in cleaving RNA, comprising
   a) creating a plurality of vectors encoding ribozymes specific for a single target RNA sequence and having differing catalytic domain sequences, which ribozymes are to be screened for effectiveness in cleaving RNA containing the target RNA sequence;
   b) providing bacterial cells that express a messenger RNA containing the target RNA sequence and that, when the messenger RNA is cleaved by one of the ribozymes, express a polypeptide that can, in sufficient quantity, cause the cells to survive in a preselected culture medium:
   c) transforming the cells with the vectors;
   d) culturing the cells in the preselected culture medium under conditions wherein the ribozymes are expressed; and
   e) selecting cells which survive.

5. The method of claim 4 wherein the cells are bacteria.

6. The method of claim 5 wherein the cells are *B. subtilis* cells.

7. The method of claim 4 wherein the vector is a plasmid.

8. The method of claim 6 wherein the polypeptide causes antibiotic resistance.

9. The method of claim 8 wherein the messenger RNA is ermC messenger RNA encoding leader and methylase polypeptides.

10. The method of claim 9 wherein synthesis of the ribozyme is under the control of an operator and inducer is added in an amount which causes only some of the cells to survive due to efficient cleavage by the ribozyme of the messenger RNA.

11. The method of claim 10 wherein the ribozyme contains a transcription terminator.

12. The method of claim 11 wherein the transcription terminator is the major rho-dependent transcription terminator of the comG gene of *B. subtilis*.

13. The method of claim 4 wherein the cell contains a single copy of the ermC gene.

14. A method for screening mutant hammerhead or hairpin ribozymes comprising culturing bacterial cells whose survival is dependent upon cleavage of a hairpin loop structure contained in messenger RNA by a ribozyme not native to the cell which cleavage alters the secondary structure of the messenger RNA to free a ribosome binding site and allow translation of a sequence of the messenger RNA coding for a polypeptide which allows the cell to survive in media in which the cell is cultured, and selecting cells which survive in order to determine the catalytic domain nucleotide sequences of the most effective ribozymes.

15. The method of claim 14 wherein the cells are bacteria.

16. The method of claim 15 wherein the bacteria are *B. subtilis* cells.

17. The method of claim 16 wherein the polypeptide causes antibiotic resistance.

18. The method of claim 17 wherein the messenger RNA is ermC messenger RNA encoding leader and methylase polypeptides.

19. The method of claim 18 wherein synthesis of the ribozyme is under the control of an operator and inducer is added in an amount which causes only some of the cells to survive due to efficient cleavage by the ribozyme of the messenger RNA.

20. The method of claim 19 wherein the ribozyme contains a transcription terminator.

21. The method of claim 20 wherein the transcription terminator is the major rho-dependent transcription terminator of the comG gene of *B. subtilis*.

22. The method of claim 21 wherein the cell contains a single copy of the ermC gene.

23. A method for screening mutant hammerhead or hairpin ribozymes for effective catalytic domains comprising culturing bacterial cells in an MLS antibiotic whose survival is dependent upon cleavage of a cleavage site contained in a hairpin loop of ermC leader messenger RNA by the ribozymes, which cleavage causes a change in structure of the ermC messenger RNA and frees a ribosome binding site to allow synthesis of methylase, thereby permitting the cell to survive in the presence of the MLS antibiotic, and selecting cells which survive.

24. The method of claim 23 wherein the ribozymes are of the Haseloff-Gerlach type.

25. The method of claim 24 wherein the cells are *B. subtilis* cells.

26. The method of claim 25 wherein synthesis of the ribozyme is under the control of an operator and inducer is added in an amount which causes only some of the cells to survive due to efficient cleavage by the ribozyme of the messenger RNA.

27. The method of claim 26 wherein the ribozyme contains a transcription terminator.

28. The method of claim 27 wherein the transcription terminator is the major rho-dependent transcription terminator of the comG gene of *B. subtilis*.

29. The method of claim 28 wherein the bacterial cell contains a single copy of the ermC gene.

30. The method of claim 24 wherein the sequence cleavable by the ribozyme is GUC, GUU or GUA.

31. The method of claim 30 wherein the sequence is GUC.

32. The method of claim 24 wherein the cleavage site is contained in a non-ermC sequence in the hairpin loop.

33. The method of claim 32 wherein the non-ermC sequence is an HIV-1 RNA sequence.

34. The method of claim 33 wherein the HIV-1 sequence is from the integrase gene.

35. The method of claim 24 wherein synthesis of the ribozyme is under the control of an inducer and inducer is added to allow survival of only cells containing the most effective ribozymes.

36. The method of claim 24 wherein the cells are cultured in media containing the MLS antibiotic tylosin.

37. A method for screening mutant Haseloff-Gerlach ribozymes comprising culturing bacterial cells in the presence of tylosin, the survival of said cells being dependent upon cleavage of a non-native cleavage site contained at about position 109 of the hairpin loop of ermC leader messenger RNA by the ribozymes inducibly expressed in the cells, which cleavage causes a change in structure of the ermC messenger RNA and frees a ribosome binding site to allow synthesis of methylase, thereby permitting the cell to survive in the media, and selecting cells which survive to determine the catalytic domain nucleotide sequence of the most effective ribozymes.

38. The method of claim 37 wherein the cells are *B. subtilis* cells.

39. The method of claim 38 wherein the expression of the ribozyme is under the control of a lac operator.

40. The method of claim 37 wherein the ribozyme is expressed by a recombinant plasmid containing a spac promoter.

41. The method of claim 40 wherein the ribozyme contains a transcription terminator.

42. The method of claim 41 wherein the transcription terminator is the major rho-dependent transcription terminator of the comG gene of *B. subtilis*.

43. The method of claim 37 wherein the sequence cleavable by the ribozyme is GUC, GUU or GUA.

44. The method of claim 37 wherein the sequence is GUC.

45. The method of claim 37 wherein the sequence in the ermC hairpin loop which contains the cleavage site is a target sequence which is not a natural ermC sequence.

46. The method of claim 45 wherein the non-ermC sequence is an HIV-1 RNA sequence.

47. The method of claim 46 wherein the HIV-1 sequence is from the integrase gene.

48. The method of claim 4 wherein the vectors contain DNA encoding ribozymes which were manufactured on a DNA synthesizer which selects nucleotide precursors from four solutions to construct the nucleotides by stepwise addition, and wherein a mixture of nucleotides is employed in at least one of the four solutions in order to randomly incorporate nucleotides during stepwise addition, resulting in generation of a variety of oligonucleotides to be screened.

49. The method of claim 48 wherein mixtures of oligonucleotide precursors are employed in all four of the solutions.

50. The method of claim 48 wherein each of the four mixtures of oligonucleotide precursors comprises about 85% wild type precursors and about 5% each of the remaining three oligonucleotide precursors.

51. The method of claim 48 wherein the cells are bacteria.

52. The method of claim 51 wherein the cells are *B. subtilis* cells.

53. The method of claim 52 wherein the vector is a plasmid.

54. The method of claim 53 wherein the polypeptide causes antibiotic resistance.

55. The method of claim 54 wherein the messenger RNA is ermC messenger RNA encoding leader and methylase polypeptides.

* * * * *

UNITED STATES PATENT AND TRADEMARK OFFICE
CERTIFICATE OF CORRECTION

PATENT NO.    : 5,616,459

DATED         : April 1, 1997

INVENTOR(S)   : Fred R. Kramer, David Dubnau, Karl A. Drlica, and Abraham Pinter It is certified that error appears in the above-identified patent and that said Letters Patent is hereby corrected as shown below:

Col. 7, line 49, change "methylass" to --methylase--.

Col. 7, line 60, change "methylass" to --methylase--.

Col. 8, line 7, change "methylass" to --methylase--.

Col. 20, claim 14, lines 29-30, change "A method for screening mutant hammerhead or hairpin ribozymes" to --A method for screening hammerhead or hairpin mutant ribozymes--.

Col. 20, claim 23, lines 61-62, change "A method for screening mutant hammerhead or hairpin ribozymes" to --A method for screening hammerhead or hairpin mutant ribozymes--.

Signed and Sealed this

Twelfth Day of October, 1999

Attest:

Q. TODD DICKINSON

*Attesting Officer*     *Acting Commissioner of Patents and Trademarks*